US012653450B2

(12) United States Patent
Ni et al.

(10) Patent No.: US 12,653,450 B2
(45) Date of Patent: Jun. 16, 2026

(54) WEARABLE SENSOR FOR CONTINUOUS MONITORING OF TISSUE MECHANICS

(71) Applicants:Duke University, Durham, NC (US); Northwestern University, Evanston, IL (US)

(72) Inventors: Xiaoyue Ni, Durham, NC (US); John A. Rogers, Evanston, IL (US); Changsheng Wu, Evanston, IL (US); Chenhang Li, Durham, NC (US)

(73) Assignees: DUKE UNIVERSITY, Durham, NC (US); NORTHWESTERN UNIVERSITY, Evanston, IL (US)

( * ) Notice: Subject to any disclaimer, the term of this patent is extended or adjusted under 35 U.S.C. 154(b) by 448 days.

(21) Appl. No.: 18/373,638

(22) Filed: Sep. 27, 2023

(65) Prior Publication Data

US 2024/0108279 A1     Apr. 4, 2024

Related U.S. Application Data

(60) Provisional application No. 63/410,429, filed on Sep. 27, 2022.

(51) Int. Cl.
*A61B 5/00* (2006.01)

(52) U.S. Cl.
CPC .............. *A61B 5/442* (2013.01); *A61B 5/002* (2013.01); *A61B 5/0022* (2013.01); *A61B 2560/0214* (2013.01); *A61B 2562/0204* (2013.01); *A61B 2562/0219* (2013.01); *A61B 2562/0261* (2013.01); *A61B 2562/028* (2013.01)

(58) Field of Classification Search
None
See application file for complete search history.

(56) References Cited

U.S. PATENT DOCUMENTS

2020/0397326 A1* 12/2020 Rogers .................. A61B 5/002
2021/0113099 A1*  4/2021 Rogers .............. A61B 5/02055

OTHER PUBLICATIONS

Wu et al. ; https://meetings.aps.org/Meeting/MAR22/Session/G00. 161; APS March Meeting 2022 vol. 67, No. 3 Monday-Friday, Mar. 14-18, 2022; Chicago (Year: 2022).*

(Continued)

*Primary Examiner* — Jay B Shah
(74) *Attorney, Agent, or Firm* — Talem IP Law, LLP

(57) ABSTRACT

A wearable device includes an elastically compliant body having a side for attaching to skin of a patient, a plurality of accelerometers for receiving acoustic wave data from acoustic waves transmitted by a transducer, a short-range radio transmitter for transmitting the acoustic wave data to a computing device, a processor for receiving the acoustic wave data from the plurality of accelerometers and providing the acoustic wave data to the short-range radio transmitter, and a battery for providing power to the processor, the plurality of accelerometers, and the short-range radio transmitter. A distance between each accelerometer of the plurality of accelerometers is predetermined. The processor, the plurality of accelerometers, the short-range radio transmitter, and the battery are embedded within the elastically compliant body.

20 Claims, 17 Drawing Sheets

(56) References Cited

OTHER PUBLICATIONS

Liu et al. Epidermal mechano-acoustic sensing electronics for cardiovascular diagnostics and human-machine interfaces; Sci. Adv. 2016;2: e1601185 (Year: 2016).*

Hirata, Kosuke, et al., "Muscle-Specific Acute Changes in Passive Stiffness of Human Triceps Surae after Stretching," European Journal of Applied Physiology, May 2016 (accessible Mar. 5, 2016), 8 pages, vol. 116, issue 5, Springer Science and Business Media LLC.

Al-Hunaidi, M. O., "Difficulties with Phase Spectrum Unwrapping in Spectral Analysis of Surface Waves Nondestructive Testing of Pavements," Canadian Geotechnical Journal, Jun. 1, 1992, 27 pages, vol. 29, issue 3, Canadian Science Publishing.

Andonian, Pierre, et al., "Shear-Wave Elastography Assessments of Quadriceps Stiffness Changes prior to, during and after Prolonged Exercise: A Longitudinal Study during an Extreme Mountain Ultra-Marathon," PLOS One, Aug. 31, 2016, p. 1-21, vol. 11, issue 8, article e0161855.

Chen, Chen, et al., "Ultrasound assessment of skin thickness and stiffness: the correlation with histology and clinical score in systemic sclerosis," Arthritis Research & Therapy, Dec. 2020 (Accessible: Aug. 26, 2020), 8 pages, vol. 22, issue 1, article 197.

Chleboun, Gary S., et al., "Relationship between muscle swelling and stiffness after eccentric exercise:," Medicine & Science in Sports & Exercise, Apr. 1, 1998, 20 pages, vol. 30, issue 4.

Coelho, Nuno Miranda, et al., "Contribution of collagen adhesion receptors to tissue fibrosis," Cell and Tissue Research, Sep. 2016 (Accessible: Jun. 28, 2016), pp. 521-538, vol. 365, issue 3.

Cui, Zequn, et al., "Haptically Quantifying Young's Modulus of Soft Materials Using a Self-Locked Stretchable Strain Sensor," Advanced Materials, Jun. 23, 2022 (Accessible: Aug. 22, 2021), pp. 1-8, vol. 34, issue 25, article 2104078.

Dagdeviren, Canan, et al., "Conformal piezoelectric systems for clinical and experimental characterization of soft tissue biomechanics," Nature Materials, Jul. 18, 2015 (accessible: May 18, 2015), pp. 728-736, vol. 14, issue 7.

Diridollou, S., et al., "In vivo model of the mechanical properties of the human skin under suction," Skin Research and Technology, Nov. 2000, pp. 214-221, vol. 6, issue 4.

Doherty, J. R., et al., "Acoustic radiation force elasticity imaging in diagnostic ultrasound," IEEE Transactions on Ultrasonics, Ferroelectrics, and Frequency Control, Apr. 2013 (Accessible Mar. 29, 2013), pp. 685-701, vol. 60,issue 4.

Feng, Xu, et al., "In vivo stiffness measurement of epidermis, dermis, and hypodermis using broadband Rayleigh-wave optical coherence elastography," Acta Biomaterialia, Jul. 1, 2022 (Accessible: Apr. 22, 2022), 25 pages, vol. 146.

Fischer-Cripps, A. C., "Critical review of analysis and interpretation of nanoindentation test data," Surface and Coatings Technology, Apr. 10, 2006 (Accessible Apr. 30, 2005), pp. 4153-4165, vol. 200, issue 14-15.

Geldof, Freija, et al., "Layer thickness prediction and tissue classification in two-layered tissue structures using diffuse reflectance spectroscopy," Scientific Reports, Feb. 1, 2022, pp. 1-12, vol. 12, article 1698.

Guimaraes, Carlos F., et al., "The stiffness of living tissues and its implications for tissue engineering," Nature Reviews Materials, Feb. 21, 2020, 60 pages, vol. 5, issue 5.

Hadavi, S., et al., "Stiff person syndrome," Practical Neurology, Sep. 14, 2011, pp. 272-282, vol. 11, issue 5.

Hu, Hongjie, et al., "Stretchable ultrasonic arrays for the three-dimensional mapping of the modulus of deep tissue," Nature Biomedical Engineering, May 1, 2023, pp. 1321-1334, vol. 7, issue 10.

Hu, Hongjie, et al., "Stretchable ultrasonic transducer arrays for three-dimensional imaging on complex surfaces," Science Advances, Mar. 23, 2018, pp. 1-11, vol. 4, issue 3, article eaar3979.

Kalli, Maria, et al., "Defining the Role of Solid Stress and Matrix Stiffness in Cancer Cell Proliferation and Metastasis," Frontiers in Oncology, Mar. 12, 2018, 7 pages, vol. 8, article 55.

Lampi, Marsha C., et al., "Targeting extracellular matrix stiffness to attenuate disease: From molecular mechanisms to clinical trials," Science Translational Medicine, Jan. 3, 2018, pp. 1-14, vol. 10, issue 422, article eaao0475.

Lee, Kunhyuck, et al., "Mechano-acoustic sensing of physiological processes and body motions via a soft wireless device placed at the suprasternal notch," Nature Biomedical Engineering, Feb. 2020 (Accessible: Nov. 25, 2019), 24 pages, vol. 4, issue 2.

Li, Chunhui, et al., "Determining elastic properties of skin by measuring surface waves from an impulse mechanical stimulus using phase-sensitive optical coherence tomography," Journal of The Royal Society Interface, May 7, 2012 (Accessible: Nov. 2, 2011), pp. 831-841, vol. 9, issue 70.

Li, Chunhui, et al., "Elastic properties of soft tissue-mimicking phantoms assessed by combined use of laser ultrasonics and low coherence interferometry," Optics Express, May 23, 2011 (Accessible: May 9, 2011), pp. 10153-63, vol. 19, issue 11.

Li, Guo-Yang, et al., "Guided wave elastography of layered soft tissues," Acta Biomaterialia, Jan. 2019 (Accessible: Dec. 5, 2018), pp. 293-304, vol. 84.

Liang, Xing, et al., "Biomechanical Properties of In Vivo Human Skin From Dynamic Optical Coherence Elastography," IEEE Transactions on Biomedical Engineering, Apr. 2010 (Accessible: Oct. 9, 2009), pp. 953-959, vol. 57, issue 4.

Liou, Hong-Cin, et al., "Mechanical Characterization of Biofilms by Optical Coherence Elastography (OCE) Measurements of Elastic Waves," 2019 IEEE International Ultrasonics Symposium (IUS), Oct. 2019, pp. 2194-2197, IEEE, Glasgow, United Kingdom.

Mariappan, Yogesh K., et al., "Magnetic resonance elastography: A review," Clinical Anatomy, Jul. 2010 (Accessible: Jun. 3, 2010), pp. 497-511, vol. 23, issue 5.

Martin, Jack A., et al., "Gauging force by tapping tendons," Nature Communications, Apr. 23, 2018, pp. 1-9, vol. 9, issue 1, article 1592.

Murphy, Matthew C., et al., "Regional brain stiffness changes across the Alzheimer's disease spectrum," NeuroImage: Clinical, Jan. 9, 2016 (accessible Dec. 19, 2015), pp. 283-290, vol. 10.

Park, Choon B., et al., "Multichannel analysis of surface waves," Geophysics, May 1, 1999, pp. 800-808, vol. 64, issue 3.

Salman, Muhammad, et al., "Assessing non-uniform stiffening of the achilles tendon noninvasively using surface wave," Journal of Biomechanics, Jan. 2019 (Accessible: Nov. 15, 2018), pp. 357-360, vol. 82.

Sanders, R., "Torsional elasticity of human skin in vivo," Pflügers Archiv European Journal of Physiology, Sep. 1973, pp. 255-260, vol. 342, issue 3.

Sigrist, Rosa M. S., et al., "Ultrasound Elastography: Review of Techniques and Clinical Applications," Theranostics, Mar. 7, 2017, pp. 1303-1329, vol. 7, issue 5.

Singh, Gurpreet, et al., "Mechanical properties of whole-body soft human tissues: a review," Biomedical Materials, Oct. 19, 2021, pp. 1-25, vol. 16, issue 6, article 062004.

Son, Donghee, et al., "Multifunctional wearable devices for diagnosis and therapy of movement disorders," Nature Nanotechnology, May 2014 (Accessible: Mar. 30, 2014), pp. 397-404, vol. 9, issue 5.

Song, Enming, et al., "Miniaturized electromechanical devices for the characterization of the biomechanics of deep tissue," Nature Biomedical Engineering, May 27, 2021, pp. 759-771, vol. 5, issue 7.

Song, Shaozhen, et al., "Shear modulus imaging by direct visualization of propagating shear waves with phase-sensitive optical coherence tomography," Journal of Biomedical Optics, Nov. 8, 2013, 8 pages, vol. 18, issue 12, article 121509.

Sun, Tao, et al., "Decoding of facial strains via conformable piezoelectric interfaces," Nature Biomedical Engineering, Oct. 22, 2020, pp. 954-972, vol. 4, issue 10.

Taljanovic, Mihra S., et al., "Shear-Wave Elastography: Basic Physics and Musculoskeletal Applications," RadioGraphics, May 11, 2017, pp. 855-870, vol. 37, issue 3.

Wang, Chonghe, et al., "Continuous monitoring of deep-tissue haemodynamics with stretchable ultrasonic phased arrays," Nature Biomedical Engineering, Jul. 16, 2021, pp. 749-758, vol. 5, issue 7.

(56)                    References Cited

OTHER PUBLICATIONS

Wang, Liyun, et al., "Quantitative Assessment of Skin Stiffness in Localized Scleroderma Using Ultrasound Shear-Wave Elastography," Ultrasound in Medicine & Biology, Jul. 2017 (Accessible: Apr. 28, 2017), pp. 1339-1347, vol. 43, issue 7.

Wells, Peter N. T., et al., "Medical ultrasound: imaging of soft tissue strain and elasticity," Journal of The Royal Society Interface, Nov. 7, 2011 (Accessible: Jun. 16, 2011), pp. 1521-1549, vol. 8, issue 64.

Yoon, Sungsoo, et al., "Near-Field Effects on Array-Based Surface Wave Methods with Active Sources," Journal of Geotechnical and Geoenvironmental Engineering, Mar. 1, 2009, pp. 399-406, vol. 135, issue 3.

Yoshitake, Yasuhide, et al., "Muscle shear modulus measured with ultrasound shear-wave elastography across a wide range of contraction intensity," Muscle & Nerve, Jul. 2014 (Accessible: Oct. 23, 2013), pp. 103-113, vol. 50, issue 1.

Zhang, Yingxuan, et al., "A Piezoelectric Tactile Sensor for Tissue Stiffness Detection with Arbitrary Contact Angle," Sensors, Nov. 18, 2020, pp. 1-14, vol. 20, issue 22, article 6607.

Yu, Xinge, et al., "Needle-Shaped Ultrathin Piezoelectric Microsystem for Guided Tissue Targeting via Mechanical Sensing," Nature Biomedical Engineering, Feb. 26, 2018, pp. 165-172, vol. 2, issue 3, Springer Science and Business Media LLC.

Gennisson, Jean-Luc, et al., "Viscoelastic and Anisotropic Mechanical Properties of in Vivo Muscle Tissue Assessed by Supersonic Shear Imaging," Ultrasound in Medicine & Biology, May 2010 (accessible Apr. 24, 2010), pp. 789-801, vol. 36, issue 5.

Brandenburg, Joline E., et al., "Ultrasound Elastography: The New Frontier in Direct Measurement of Muscle Stiffness," Archives of Physical Medicine and Rehabilitation, Nov. 2014 (accessible Jul. 23, 2014), 23 pages, vol. 95, issue 11.

Geerligs, Marion, et al., "In Vitro Indentation to Determine the Mechanical Properties of Epidermis," Journal of Biomechanics, Apr. 2011 (accessible Feb. 5, 2011), pp. 1176-1181, vol. 44, issue 6.

Störchle, Paul, et al., "Measurement of Mean Subcutaneous Fat Thickness: Eight Standardised Ultrasound Sites Compared to 216 Randomly Selected Sites," Scientific Reports, Nov. 2, 2018, vol. 8, issue 1, Springer Science and Business Media LLC.

Joodaki, Hamed, et al., "Skin Mechanical Properties and Modeling: A Review," Proceedings of the Institution of Mechanical Engineers, Part H: Journal of Engineering in Medicine, Apr. 2018 (accessible Mar. 5, 2018), 21 pages, vol. 232, issue 4, SAGE Publications.

Delalleau, A., et al., "A Nonlinear Elastic Behavior to Identify the Mechanical Parameters of Human Skin in Vivo," Skin Research and Technology, May 2008 (accessible Jul. 27, 2007), pp. 152-164, vol. 14, issue 2, Wiley.

A, Kalra, et al., "Mechanical Behaviour of Skin: A Review," Journal of Material Science & Engineering, 2016, 7 pages, vol. 5, issue 4, article 1000254, OMICS Publishing Group.

* cited by examiner

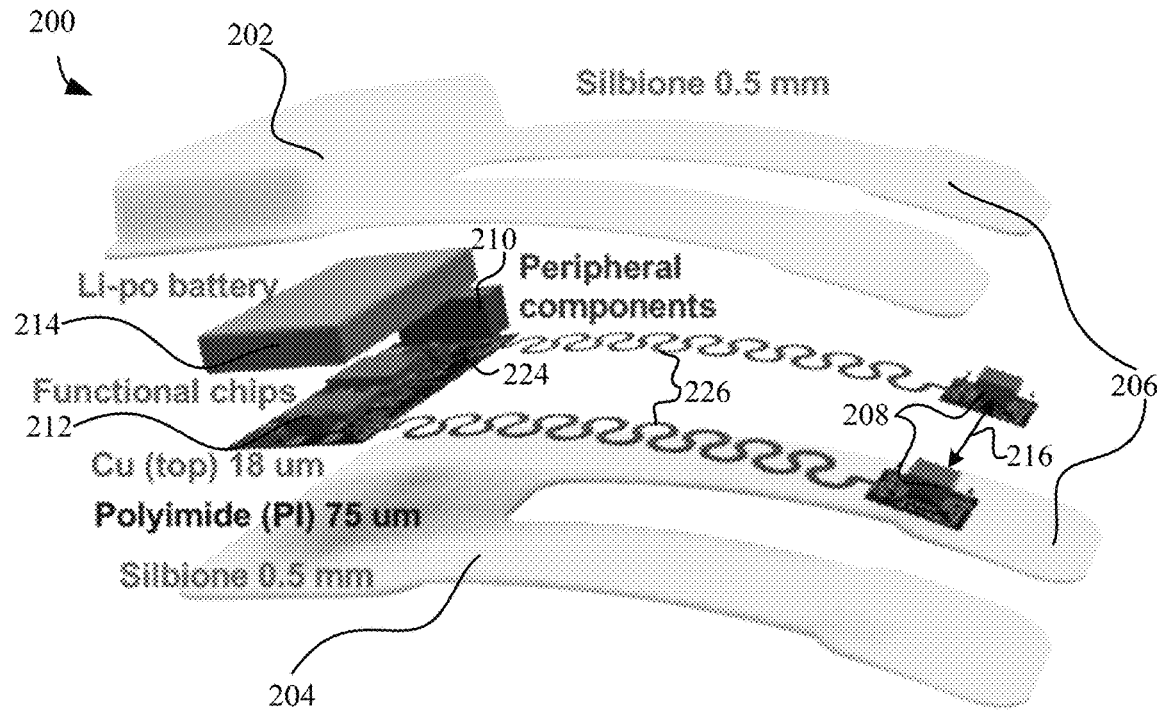
Figure 2A
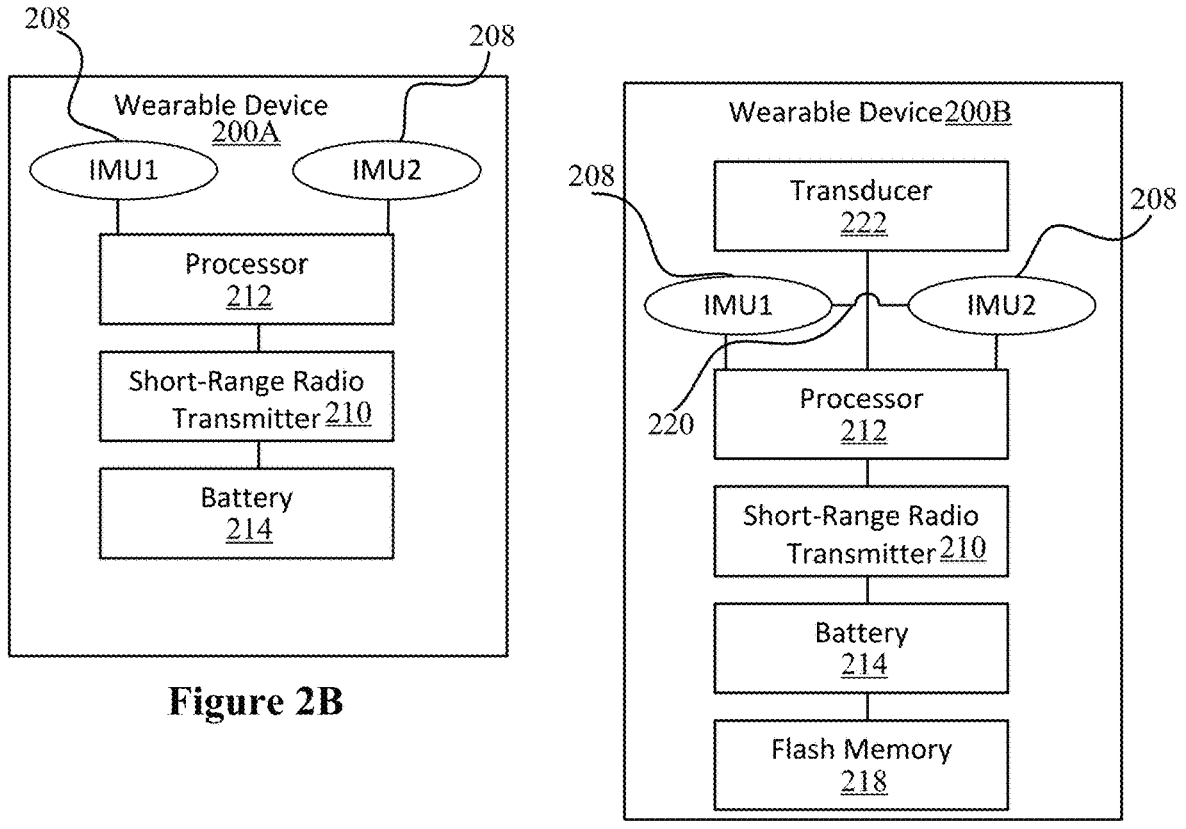
Figure 2B
Figure 2C

300

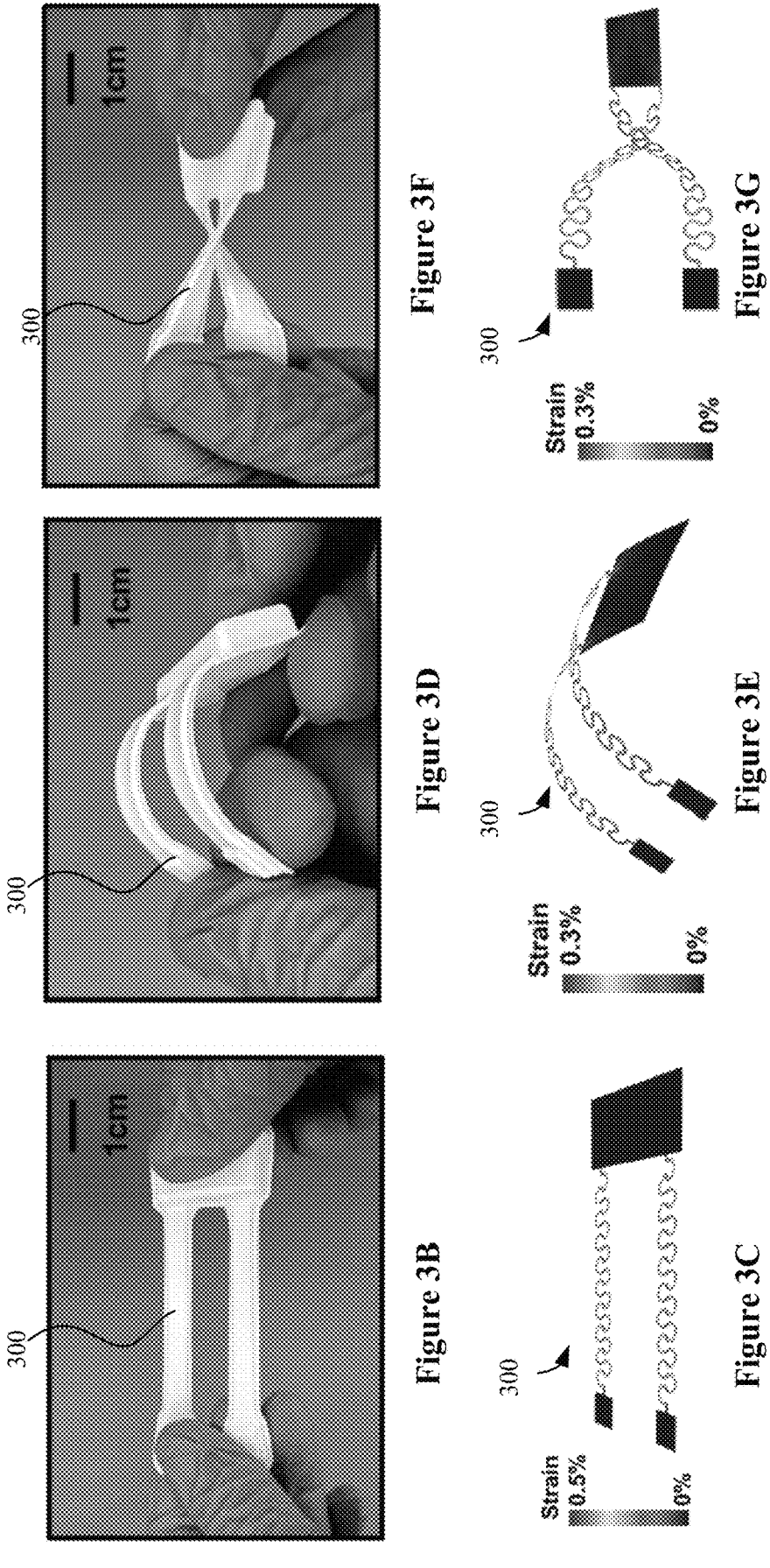

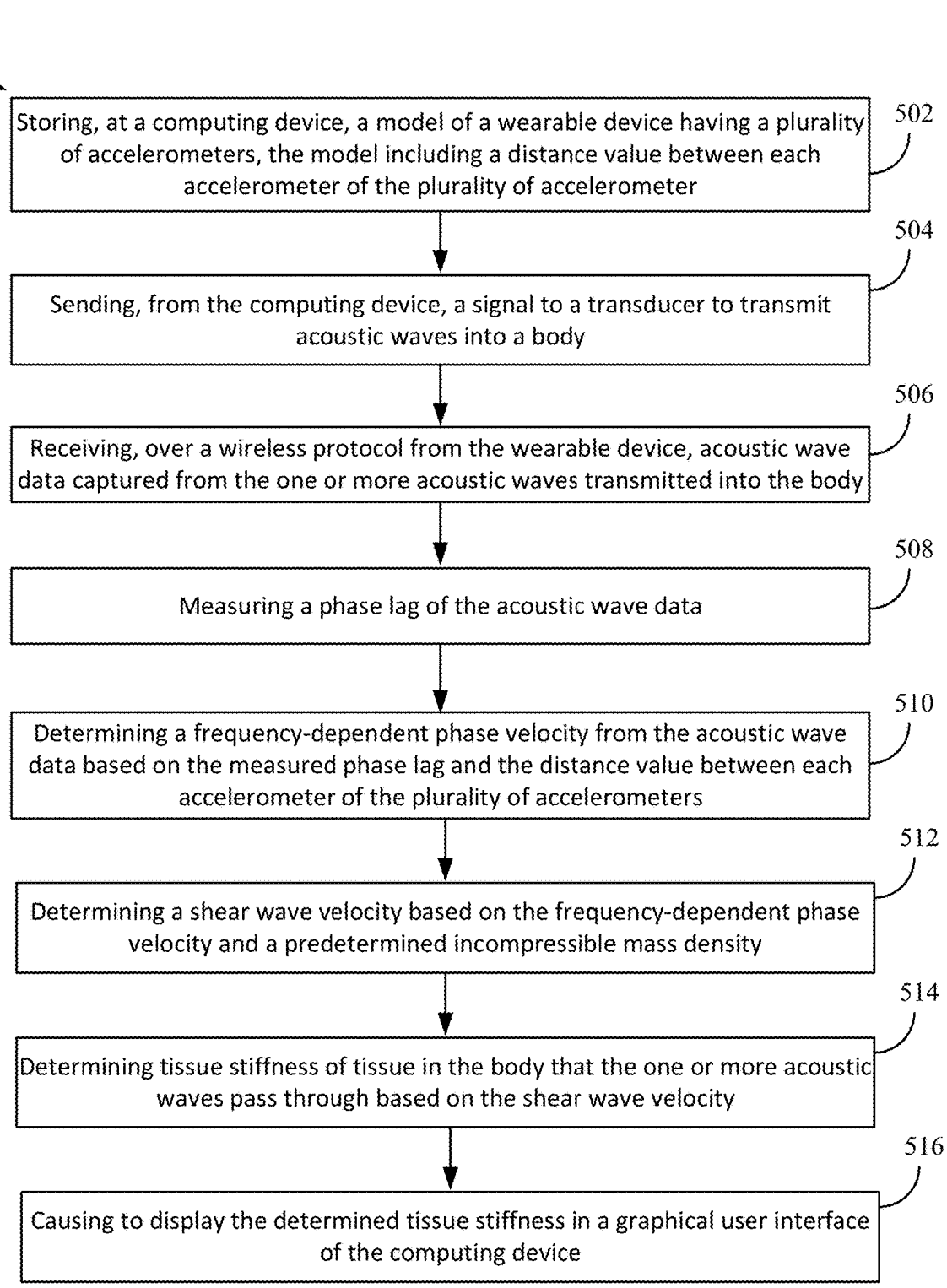

500

502
Storing, at a computing device, a model of a wearable device having a plurality of accelerometers, the model including a distance value between each accelerometer of the plurality of accelerometer 504
Sending, from the computing device, a signal to a transducer to transmit acoustic waves into a body 506
Receiving, over a wireless protocol from the wearable device, acoustic wave data captured from the one or more acoustic waves transmitted into the body 508
Measuring a phase lag of the acoustic wave data 510
Determining a frequency-dependent phase velocity from the acoustic wave data based on the measured phase lag and the distance value between each accelerometer of the plurality of accelerometers 512
Determining a shear wave velocity based on the frequency-dependent phase velocity and a predetermined incompressible mass density 514
Determining tissue stiffness of tissue in the body that the one or more acoustic waves pass through based on the shear wave velocity 516
Causing to display the determined tissue stiffness in a graphical user interface of the computing device

Figure 5

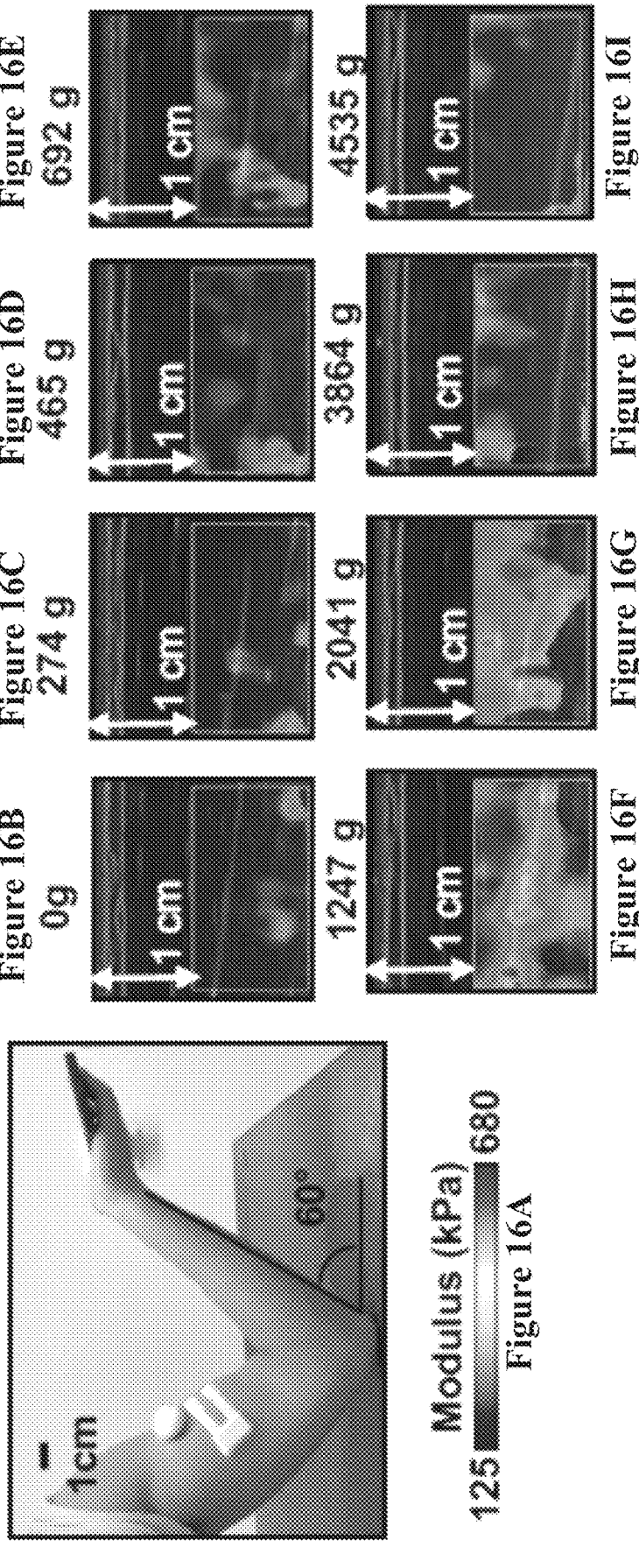

WEARABLE SENSOR FOR CONTINUOUS MONITORING OF TISSUE MECHANICS

CROSS-REFERENCE TO RELATED APPLICATIONS

This application claims the benefit of U.S. Provisional Application Ser. No. 63/410,429, filed Sep. 27, 2022.

BACKGROUND

Tissue stiffness fundamentally influences the functionality of biological tissues. Disease such as a lesion often presents with changes in tissue stiffness. Other examples include aberrant accumulation of connective tissue in response to injury or damage in fibrosis, unusual cell proliferation and tumor growth in cancer, asymmetric or localized muscle deactivation in neurological disorders, and peripheral edema in diabetes and cardiovascular diseases. Monitoring these changes in various settings, such as an ambulatory or sports medicine setting, can provide critical insights into wound healing, disease progression, and/or treatment effectiveness.

Prior solutions for characterizing tissue stiffness primarily utilizes point-of-care techniques that involve a tradeoff between accuracy and ease of use. For example, physical palpation (e.g., a physician using their hand) is straightforward to perform but is highly subjective. Mechanical testing methods (e.g., indentation, torsion, tension, and suction) allow for non-invasive and quantitative assessments of tissue stiffness, but depend heavily on quality of calibration and operation for accurate results. Furthermore, most of these surface methods have limited probing depth (e.g., 1 cm or less).

Elastography offers accurate and depth-sensitive measurements of tissue stiffness by examining characteristics of elastic wave propagation via ultrasound, magnetic resonance imaging, and/or optical topography. However, while there is a great amount of information of tissue mechanics encoded in the measured wave dispersion relationship, existing elastography technologies necessitate complex setups and highly skilled practitioners that result in high barriers from deployment in many settings (e.g., ambulatory monitoring setting). In addition, the typically rigid form factors of the devices require considerable engineering effort to maintain stable interfacial contacts that restrict the placement of the corresponding devices to anatomical sites with minimal curvatures.

Recent advancements in wearable devices have enabled conformal sensing of skin vibrations and tissue acoustics. For example, miniaturized devices based on vibrational mechanics to characterize superficial tissues (e.g., <1 cm) have been created. Skin-mounted devices that probe wave mechanics (i.e., elastography) allow for deep tissue (e.g., >1 cm) sensing. For example, detecting shear wave propagation in tendons using a pair of wearable inertial measurement units (IMUs) can assess differences in tendon stiffness. Stretchable ultrasonic arrays have even enabled three-dimensional modulus mapping of deep tissue. However, these wearable technologies encounter limited usability in certain settings (e.g., ambulatory settings) due to their dependency on tethered power transmission and/or data acquisition systems that handle complex and resource demanding back-end tasks (e.g., algorithmic computation).

BRIEF SUMMARY

A wearable sensor for continuous monitoring of tissue mechanics and methods of using the wearable sensor are provided herein. Advantageously, due to the wireless functionality and computationally light algorithm employed, the device requires no calibration to be used on a patient. Furthermore, due to these advantages and the elastically compliant body, the wearable sensor provides the ability to monitor tissue mechanics in a variety of settings (e.g., ambulatory and/or sports medicine).

A wearable device includes an elastically compliant body having a side for attaching to skin of a patient, a plurality of accelerometers for receiving acoustic wave data from acoustic waves transmitted by a transducer, a short-range radio transmitter for transmitting the acoustic wave data to a computing device, a processor for receiving the acoustic wave data from the plurality of accelerometers and providing the acoustic wave data to the short-range radio transmitter, and a battery for providing power to the processor, the plurality of accelerometers, and the short-range radio transmitter. A distance between each accelerometer of the plurality of accelerometers is predetermined. The processor, the plurality of accelerometers, the short-range radio transmitter, and the battery are embedded within the elastically compliant body.

In some cases, the wearable device further includes a strain gauge that is coupled to each of the plurality of accelerometers for measuring real-time distance between each of the plurality of accelerometers. In some cases, the wearable device further includes a memory for on-board storage of the acoustic wave data received by the plurality of accelerometers. In some cases, the short-range radio transmitter and the processor are part of a System-on-Chip. In some cases, the wearable device further includes the transducer for transmitting the acoustic waves. In some cases, the transducer is embedded within the elastically compliant body at second distance from the plurality of accelerometers that is predetermined. In some cases, the transducer is an audio exciter. In some cases, the device includes more than one transducers.

A system includes a transducer for transmitting acoustic waves, a wearable device, and one or more storage media having instructions stored thereon that when executed by a processing system, direct the processing system to at least: store, at a computing device, a model of a wearable device having a plurality of accelerometers, send, from the computing device, a signal to a transducer to transmit acoustic waves into a body, receive, over a wireless protocol from the wearable device, acoustic wave data captured from the acoustic waves transmitted into the body, measure a phase lag of the acoustic wave data, determine a frequency-dependent phase velocity from the acoustic wave data based on the measured phase lag and a distance value between each accelerometer of the plurality of accelerometers of the wearable device, determine a shear wave velocity based on the frequency-dependent phase velocity and a predetermined incompressible mass density, determine tissue stiffness of tissue in the body that the acoustic waves pass through based on the shear wave velocity, and cause to display the determined tissue stiffness in a graphical user interface of the computing device. The model includes the distance value between each accelerometer of the plurality of accelerometers.

In some cases, the model is updated with a real-time distance value between each accelerometer of the plurality of accelerometers while the wearable device is in use. In some cases, no calibration to the wearable device is required to determine the tissue stiffness.

A method includes storing, at a computing device, a model of a wearable device having a plurality of accelerometers, sending, from the computing device, a signal to a transducer to transmit acoustic waves into a body, receiving, over a wireless protocol from the wearable device, acoustic wave data captured from the acoustic waves transmitted into the body, measuring a phase lag of the acoustic wave data, determining a frequency-dependent phase velocity from the acoustic wave data based on the measured phase lag and a distance value between each accelerometer of the plurality of accelerometers of the wearable device, determining a shear wave velocity based on the frequency-dependent phase velocity and a predetermined incompressible mass density, determining tissue stiffness of tissue in the body that the acoustic waves pass through based on the shear wave velocity, and causing to display the determined tissue stiffness in a graphical user interface of the computing device. The model includes a distance value between each accelerometer of the plurality of accelerometers.

In some cases, the tissue stiffness is determined in real time and displayed in real time over a time period. In some cases, the wearable device is attached to skin of a patient that is engaged in physical activity or in an ambulatory setting. In some cases, the wireless protocol is Bluetooth Low Energy protocol. In some cases, the model is updated while the wearable device is in use. In some cases, the update to the model is an update to the distance value between each accelerometer of the plurality of accelerometers sent from the wearable device.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIG. 2A illustrates an exploded view of a wearable device.

FIGS. 2B and 2C illustrate block diagrams of a wearable device.

FIGS. 3B and 3C illustrate views of a wearable device being stretched.

FIGS. 3D and 3E illustrate views of a wearable device being bent.

FIGS. 3F and 3G illustrate views of a wearable device being twisted.

FIG. 5 illustrates a flow diagram of the operations performed by a tissue elasticity measurement system.

FIG. 16A illustrates an experimental setup.

FIGS. 16B-16I illustrate the corresponding ultrasound images of the tissue underneath the sensor when the subject holds different weights.

DETAILED DESCRIPTION

A wearable sensor for continuous monitoring of tissue mechanics and methods of using the wearable sensor are provided herein. Advantageously, due to the wireless functionality and computationally light algorithm employed, the device requires no calibration to be used on a patient. Furthermore, due to these advantages and the elastically compliant body, the wearable sensor provides the ability to monitor tissue mechanics in a variety of settings (e.g., ambulatory and/or sports medicine).

Figures 1A, 1B:
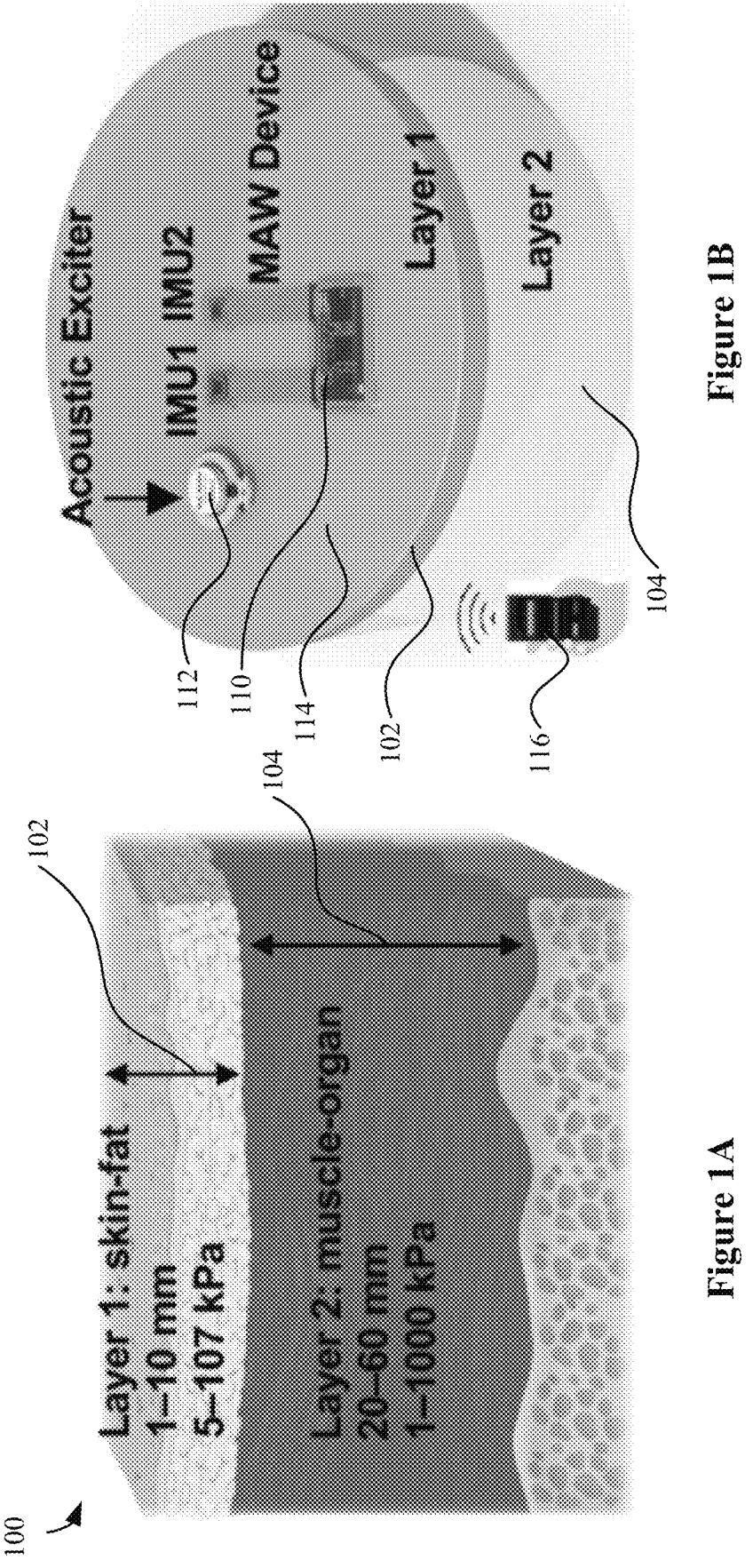
FIG. 1A illustrates a cross-section of a skin-fat layer over underlying muscle and organ tissues.
FIG. 1B illustrates a wearable device attached to the surface of the skin-fat layer.

FIG. 1A illustrates a cross-section of a skin-fat layer over underlying muscle and organ tissues. Referring to FIG. 1A, a body 100 of a patient includes a skin-fat tissue layer 102 and a muscle-organ tissue layer 104. FIG. 1B illustrates a wearable device attached to the surface of the skin-fat layer. Referring to FIG. 1B, a wearable device 110 and a transducer 112 are positioned on the surface 114 of the skin-fat tissue layer 102. When initialized (e.g., wirelessly) by a remote computing device 116, the transducer 112 transmits acoustic waves into the body 100, including the skin-fat tissue layer 102 and the muscle-organ tissue layer 104.

Acoustic wave data (e.g., of the acoustic waves transmitted into the body 100 by the transducer 112) is received by the wearable device 110 and sent (e.g., wirelessly) to the remote computing device 116.

FIG. 2A illustrates an exploded view of a wearable device. FIGS. 2B and 2C illustrate a block diagrams of a wearable device. Referring to FIG. 2A, a wearable device 200 includes a top portion 202 and a bottom portion 204 of an elastically compliant body 206. Referring to FIGS. 2A-2C, embedded within the elastically compliant body 206 of the wearable device 200, 200A, 200B are a plurality of accelerometers 208 for receiving acoustic wave data from acoustic waves transmitted by a transducer, a short-range radio transmitter 210 for transmitting the acoustic wave data to a remote computing device, a processor 212 for receiving the acoustic wave data from the plurality of accelerometers 208, and a battery 214 for providing power to the processor 212, the plurality of accelerometers 208, and the short-range radio transmitter 210. A distance 216 between each accelerometer of the plurality of accelerometers 208 is predetermined (e.g., 2 cm). In some cases, a transducer is also included. In some cases, a plurality of transducers are included.

Referring to FIGS. 2A and 2C, a memory 218 is also embedded within the elastically compliant body 206 for on-board storage of the acoustic wave data received by the plurality of accelerometers 208. In some cases, the memory 218 is a flash memory (W25Q128, Winbond). In some cases, the short-range radio transmitter 210 and the processor 212 are part of a System-on-Chip. In some cases, the System-on-Chip is a Radio Frequency System-on-Chip (nRF52832, Nordic Semiconductor) for data acquisition, control, and wireless communication through Bluetooth Low-Energy (BLE) protocols. In some cases, a strain gauge 220 (not included in the embodiment illustrated in FIG. 2A) is coupled to each of the plurality of accelerometers 208 for measuring real-time distance between each of the plurality of accelerometers 208.

In some cases, the transducer 222 (not included in the embodiment illustrated in FIG. 2A) that transmits the acoustic waves into the body is also embedded in the elastically compliant body 206 of the wearable device 200B. In some cases, the transducer is embedded within the elastically compliant body 206 at a second distance (e.g., 2 cm) from the plurality of accelerometers that is predetermined. In some cases, the transducer 222 is an audio exciter (ASX02604-R, PUI Audio; diameter=26.5 mm, weight=10 g). In some cases, a plurality of transducers are included. In some cases, the plurality of transducers transmit different frequencies from one another, which are received by the plurality of accelerometers. In some cases, a distance between the plurality of transducers and/or the plurality of accelerometers is known and/or predetermined.

Referring to FIG. 2A, in some cases, the elastically compliant body 206 is a medical grade silicone elastomer (Silibrone RTV 4420, Elkem; part A and part B, mixed with 3% of Silc-Pig white silicone dye) or other similar material that provides elastically compliant attributes. In some cases, the elastically compliant body 206 is 0.5 mm thick. In some cases, the elastically compliant body 206 is soft (540 kPa). In some cases, the elastically compliant body 206 is waterproof.

In some cases, the top portion 202 and the bottom portion 204 are coupled to one another to form the elastically compliant body 206. In some cases, the top portion 202 and the bottom portion 204 are monolithic. For example, the elastically compliant body may be formed as a single structure around the internal components (e.g., the plurality of accelerometers 208, the short-range radio transmitter 210, the processor 212, the battery 214, and/or the memory 218) of the wearable device 200. In some cases, the bottom side 204 of the elastically compliant body 206 is configured to attach to the skin of a patient (e.g., via an adhesive or any other attachment mechanism utilized for attachment to skin).

In some cases, the internal components (e.g., as described above) are electrically coupled via a flexible printed circuit board (fPCB) 224 middle polyimide layer (e.g., 75 μm thick) sandwiched between two patterned copper traces 226 (18 μm thick). In some cases, the plurality of accelerometers 208 are digital inertial measurement units (MPU9250, InvenSense). In some cases, the battery 214 is a rechargeable 60 mAh lithium-ion polymer battery supported by a wireless charging unit for power supply. In some cases, the two patterned copper traces 226 electrically couple the plurality of accelerometers 208 on separate fPCB islands with the other internal components on the main fPCB 224, while attenuating mechanical disturbances from tethering. In some cases, the plurality of accelerometers 208 is an array of accelerometers (e.g., accelerometers in the X and Y direction) with known spacing between each of the accelerometers in the array of accelerometers. In some cases, the array of accelerometers permits 3D elastography.

Figure 3A:
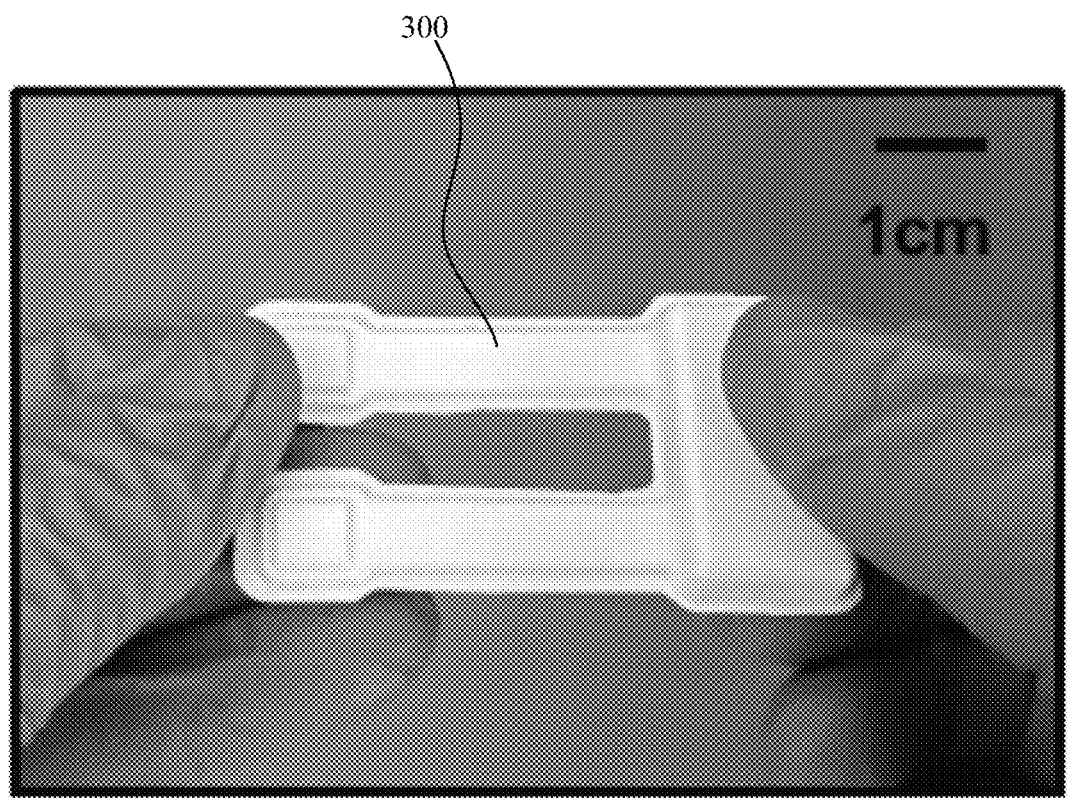
FIG. 3A illustrates an undeformed view of a wearable device.

FIG. 3A illustrates an undeformed view of a wearable device. Referring to FIG. 3A, the wearable device 300 may further include a medical-grade double-sided silicone/acrylate adhesive (2477P, 3M) to ensure a gentle and secure affixation of the wearable device 300 to the skin of a patient.

FIGS. 3B and 3C illustrate views of a wearable device being stretched. FIGS. 3D and 3E illustrate views of a wearable device being bent. FIGS. 3F and 3G illustrate views of a wearable device being twisted. Referring to FIGS. 3B-3G, the wearable device 300 maintains its functionality under different modes of mechanical loading, including but not limited to stretching (<20%) as illustrated in FIGS. 3B and 3C, bending (<60°) as illustrated in FIGS. 3D and 3E, and twisting (<120°) as illustrated in FIGS. 3F and 3G. Finite Element Analysis confirms that the maximum strain in the copper layer stays within the fracture limit (ε=1%) under all conditions and verifies that the interfacial stresses on the wearable device 300 and skin stay below human sensation threshold (~20 kPa).

Figure 4:
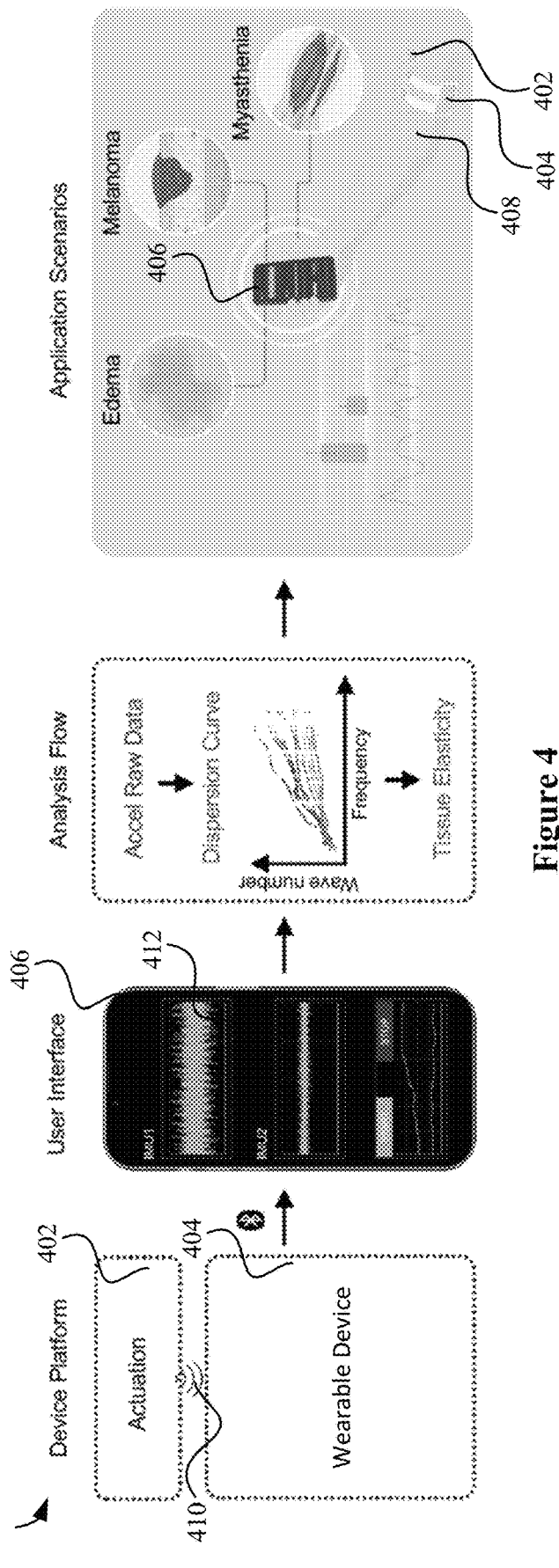
FIG. 4 illustrates a block diagram outlining the operational flow of a tissue elasticity measurement system.

FIG. 4 illustrates a block diagram outlining the operational flow of a tissue elasticity measurement system. FIG. 5 illustrates a flow diagram of the operations performed by a tissue elasticity measurement system. Referring to FIGS. 4 and 5, a tissue elasticity measurement system 400 includes a transducer 402, a wearable device 404, and a remote computing device 406 that performs a method 500 of measuring tissue elasticity of tissue within a body 408. The transducer 402, the wearable device 404, and the remote computing device 406 may include any combination of the features described above with respect to FIGS. 1A-3G.

The method 500 includes storing (502), at the remote computing device 406, a model of a wearable device 404 having a plurality of accelerometers. The model includes a distance value between each accelerometer of the plurality of accelerometers. In some cases, the distance value is the same between each of the plurality of accelerometers (e.g., 2 cm). In some cases, the distance value varies between each of the plurality of accelerometers (e.g., between 1 cm and 10 cm). In some cases, the model is part of an application running on the remote computing device 406. In some cases, the model is updated (e.g., in real-time) while the wearable device 404 is in use. In some cases, the update to the model is an update to the distance value between each accelerometer of the plurality of accelerometers (e.g., via a strain gauge to account for stretching, bending, and/or twisting of the wearable device 404) sent from the wearable device 404. In some cases, the wearable device 404 is attached to skin of a patient (e.g., the patient's body 408) that is engaged in physical activity or in an ambulatory setting.

The method 500 further includes sending (504), from the remote computing device 406, a signal to the transducer 402 to transmit acoustic waves 410 into a body 408, and receiving (506), over a wireless protocol from the wearable device 404, acoustic wave data captured from the acoustic waves 410 transmitted into the body 408. In some cases, the transducer 402 is embedded within (e.g., and apart of) the wearable device 404. In some cases, the wireless protocol is Bluetooth Low Energy (BLE) protocol. In some cases, the wireless protocol is another type of wireless protocol, such as for example, Wi-Fi, or Zigbee.

The method 500 further includes (e.g., at the remote computing device 406/an application running on the remote computing device 406) measuring (508) a phase lag of the acoustic wave data, determining (510) a frequency-dependent phase velocity from the acoustic wave data based on the measured phase lag and the distance value between each accelerometer of the plurality of accelerometers of the wearable device 404, determining (512) a shear wave velocity based on the frequency-dependent phase velocity and a predetermined incompressible mass density, determining (514) tissue stiffness of tissue in the body 408 that the acoustic waves 410 pass through based on the shear wave velocity, and causing (516) to display the determined tissue stiffness in a graphical user interface 412 of the remote computing device 406.

In some cases, the tissue stiffness is determined (514) in real-time and displayed in real-time over a time period (e.g., a predetermined period of time and/or as long as the user of the remote computing device 406 is using the application. In some cases, no calibration to the wearable device 404 is required to determine the tissue stiffness. This provides a significant advantage over other systems in sports medicine and ambulatory settings by allowing users to use the device quickly while still receiving accurate results without the normal calibration required in other devices. Indeed, normal calibration required by other devices and systems takes time and effort that may not be feasible in an ambulatory setting or may be undesirable in a sports medicine setting.

Figures 6A, 6B:
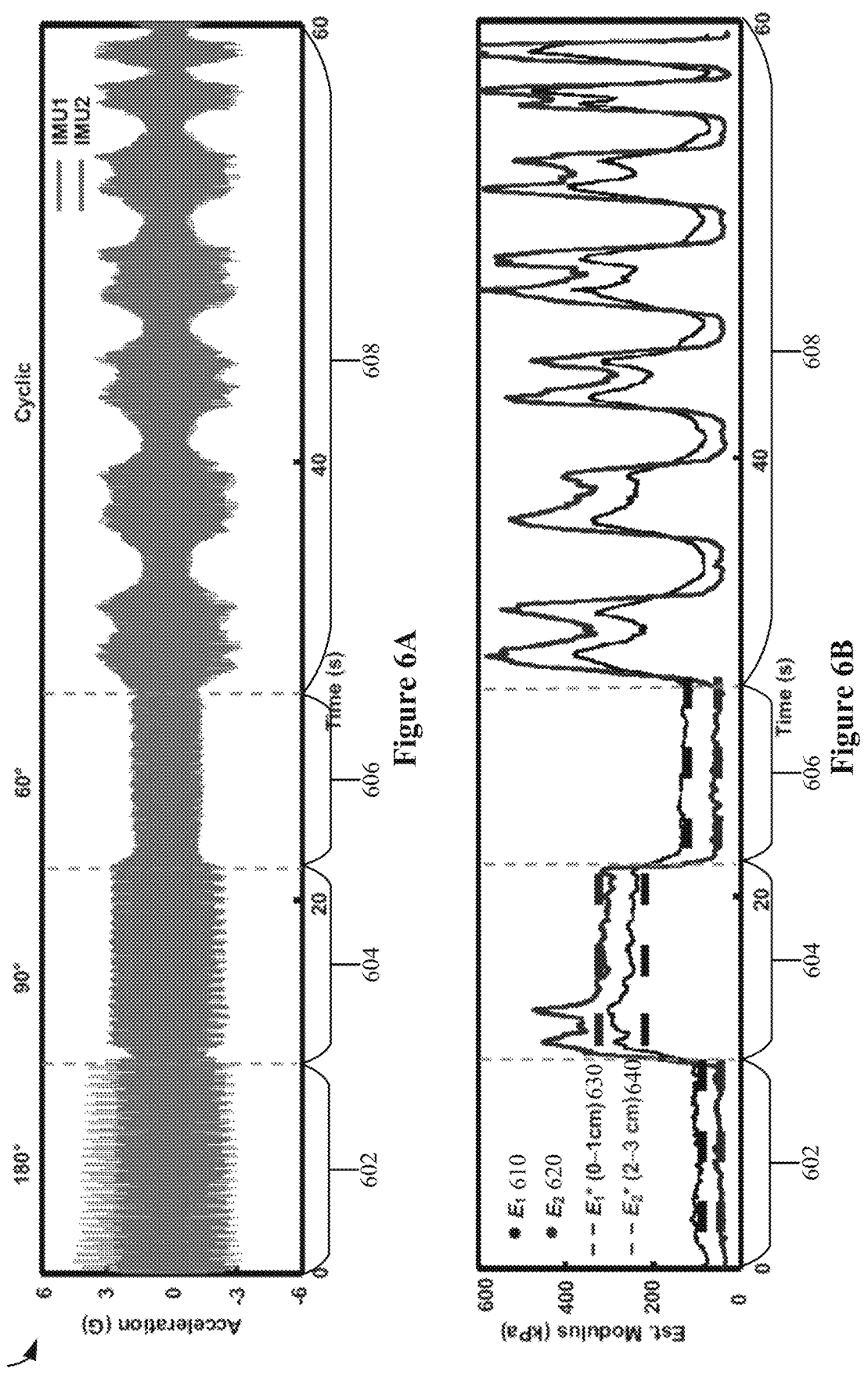
FIG. 6A illustrates an example of acoustic wave data captured during an experiment.
FIG. 6B illustrates an example display of tissue stiffness determined from the acoustic wave data of FIG. 5.

FIG. 6A illustrates an example of acoustic wave data captured by a wearable device during an experiment. Referring to FIG. 6A, a graphical representation of acoustic wave data 600 over time was captured by the wearable device having two accelerometers (e.g., IMU1 and IMU2) during an experiment in which a subject/patient held a dumbbell in a relaxed position for 10 seconds (as represented in Zone A 602 of the acoustic wave data), followed by holding the dumbbell in a half-curled (e.g., 90°) position for another 10 seconds (as represented in Zone B 604 of the acoustic wave data), followed by a holding the dumbbell in a curled (e.g., 60°) for another 10 seconds (as represented in Zone C 606 of the acoustic wave data), followed by seven cycles of curls using the dumbbell for a final 30 seconds (as represented in Zone D 608 of the acoustic wave data).

FIG. 6B illustrates an example display of tissue stiffness determined from the acoustic wave data of FIG. 6A. Referring to FIG. 6B, a first line 610 $E_1$ represents the tissue stiffness of tissue at a depth of 0-10 mm through Zones A-D 602, 604, 606, 608. A second line 620 $E_2$ represents the tissue stiffness of tissue at a depth of 20-30 through Zones A-D 602, 604, 606, 608. A third line 630 $E_1$* represents the tissue stiffness of tissue at a depth of 0-10 mm through Zones A-C 602, 604, 606. A fourth line 640 $E_2$* represents the tissue stiffness of tissue at a depth of 20-30 mm through Zones A-C 602, 604, 606. The first line 610 $E_1$ and the second line 620 $E_2$ were determined via a wearable device and corresponding remote computing device via method 500. The third line 630 $E_1$* and the fourth line 640 $E_2$* were determined via use of traditional shear wave elastography. It should be noted that the tissue stiffness represented by the third line 630 $E_1$* and the fourth line 640 $E_2$* could not be determined for Zone D 608 because traditional shear wave elastography is not capable of accurate determinations of moving objects (e.g., such as the seven cycles of curls using the dumbbell for the final 30 seconds as represented in Zone D 608 of the acoustic wave data).

FIG. 6B also represents an example of a display of the determined tissue stiffness in a graphical user interface of a remote computing device, except the third line 630 $E_1$* and the fourth line 640 $E_2$* would not be present.

Figure 7:
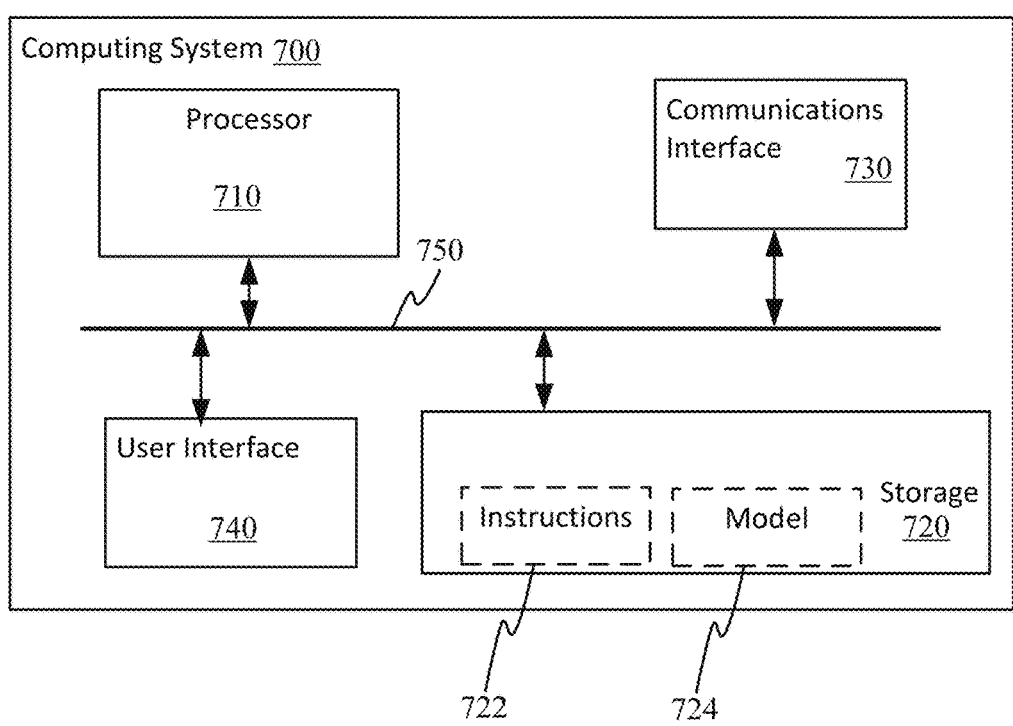
FIG. 7 illustrates a block diagram of a remote computing device.

FIG. 7 illustrates a block diagram of a remote computing device. The remote computing device 700 can be used for performing the method 500. Referring to FIG. 7, a computing system 700 can include a processor 710, storage 720, a communications interface 730, and a user interface 740 coupled, for example, via a system bus 750. Processor 710 can include one or more of any suitable processing devices ("processors"), such as a microprocessor, central processing unit (CPU), graphics processing unit (GPU), field programmable gate arrays (FPGAs), application-specific integrated circuits (ASICs), logic circuits, state machines, application-specific standard products (ASSPs), system-on-a-chip systems (SOCs), complex programmable logic devices (CPLDs), etc.

Storage 720 can include any suitable storage media that can store instructions 722 for performing any method or process described herein, including method 500 of FIG. 5 and/or any method or process for determining tissue stiffness. Storage 720 also includes the model 724 of the wearable device that is used to carry out instructions 722 for performing the method 500 of FIG. 5. Suitable storage media for storage 720 include random access memory, read only memory, magnetic disks, optical disks, CDs, DVDs, flash memory, magnetic cassettes, magnetic tape, magnetic disk storage or other magnetic storage devices, or any other suitable storage media. As used herein "storage media" do not consist of transitory, propagating waves. Instead, "storage media" refers to non-transitory media.

Communications interface 730 can include wired or wireless interfaces for communicating with the wearable device as well as interfaces for communicating with the "outside world" (e.g., external networks). User interface 740 can include a display on which the determined tissue stiffness and any other relevant information can be displayed as well as suitable input device interfaces for receiving user input (e.g., mouse, keyboard, microphone).

Experiment

The inventors conducted an experiment by following a process similar to method 500 described in FIG. 5. Although this experiment is limited to the determination of tissue stiffness during physical activity, as explained above, determination of tissue stiffness in other settings using the methods described herein are within the scope of this invention.

The inventors used a wireless mechano-acoustic wave (MAW) sensing system for wearable elastography. The MAW device (e.g., similar to the device described with respect to FIG. 2A) was optimized for intimate interface with the test subject's skin and incorporated a pair of MEMS-based accelerometers to probe broadband (e.g., 50-800 Hz) acoustic waves initiated by a skin-mounted exciter. A calibration-free algorithm that leveraged the spectral analysis of surface waves computed the depth-dependent Young's modulus from the measured dispersion relationship. The tests on diverse tissue-like phantoms (with Young's modulus, E, ranging from 88 to 1532 kPa) showed an estimation error of less than 10% when compared with standard measurements from tensile tests. The measurement depth of soft tissues, which varies with the wavelengths, is approximately 2-46 mm. The range was associated with the actuation frequency of 50-800 Hz and the stiffness of the target materials. The system used demonstrated the ability to track the softening of porcine tissues upon injection of a phosphate buffered saline (PBS) solution, as well as stiffening of the human skeletal muscles under increasing tension. Ultrasound elastography measurements, conducted in parallel during quasi-static conditions, validated the device performance. A real-time assessment of bi-layer stiffness of biceps and rectus femoris muscles during physical activities showcased the capability of the system for continuous monitoring in the ambulatory environment.

In the experiment, the MAW sensor was used with an acoustic exciter and a smart device. The smart device included a customized app for wireless control and data transfer with the MAW sensor and the acoustic exciter. Customized spectral analysis algorithms compute the frequency-dependent phase velocity from the broadband signals (e.g., the dispersion relation) and estimate the tissue modulus using a scaling law derived from finite element analysis (FEA) predictions. This integrated hardware and software platform provides a quantitative basis for real-time, ambulatory monitoring of tissue elasticity.

Figure 8:
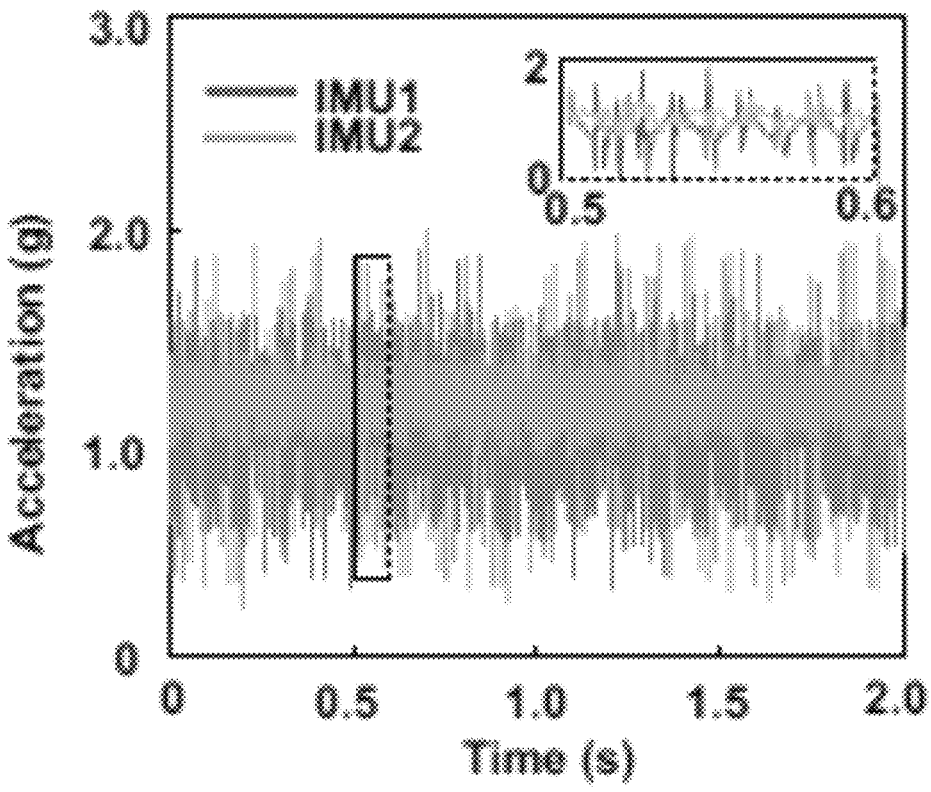
FIG. 8 illustrates a sample 2-second data measured from a representative bi-layer material.

19 phantom materials, denoted as M1-M19, were made by stacking two layers of elastomers with varied stiffness and thickness, leading to a similar mass density (e.g., 1.03-1.08 g/cm$^3$) but a wide spectrum of Young's modulus in two layers (e.g., Layer 1: 88-1532 kPa, 10 mm thick; Layer 2: 84-732 kPa, 10/80 mm thick). The two separate layers in phantom materials simulate a bi-layer, homogeneous tissue model representing the skin-fat and muscle-organ layers. The two umbilical accelerometers were positioned 20 mm apart (e.g., with the distance gauged by a ruler). The accelerometers measured vibrations with a sampling frequency of 1600 Hz, a resolution of 14 bits, and a dynamic range of ±8 g (where g was the gravitational acceleration, 9.8 m/s$^2$). The audio exciter was in line with the two accelerometers to reduce the near-field effects which refer to the interference from body waves on surface wave measurements. A wireless Bluetooth receiver (Soundsync A3352, Anker) transmitted to the audio exciter an audio signal that combined sinusoidal waves with frequencies that ranged from 50 Hz to 800 Hz at an interval of 10 Hz. FIG. 8 illustrates a sample 2-second data measured from a representative bi-layer material, M2 (e.g., Layer 1: 147 kPa, 10 mm thick; Layer 2: 88 kPa, 80 mm thick).

Figure 9:
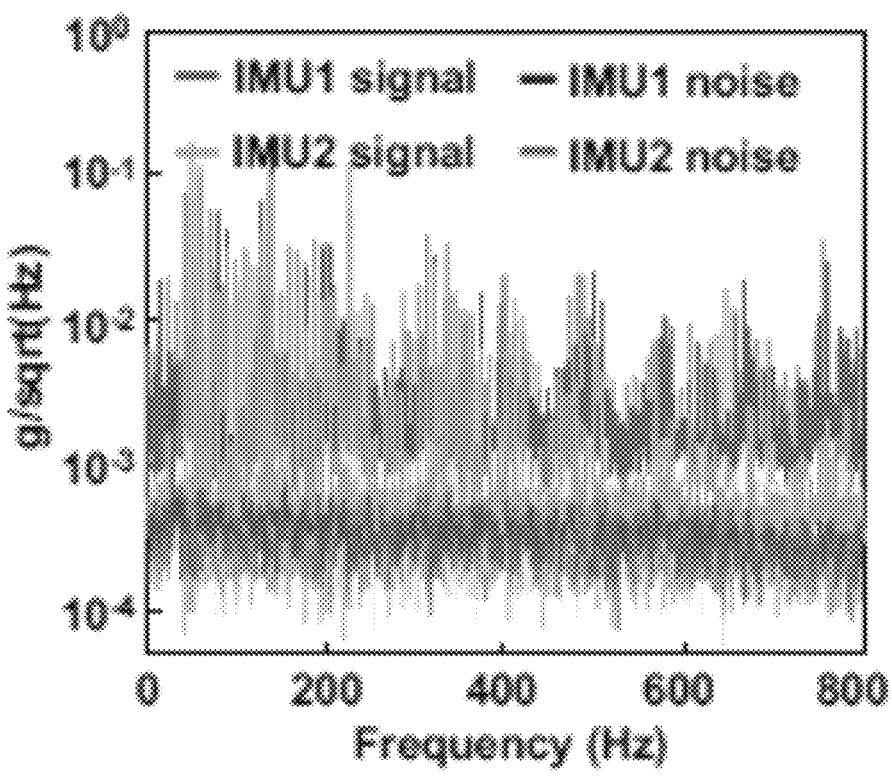
FIG. 9 illustrates power spectral analysis of the typical noise floor of the MAW sensor.

FIG. 9 illustrates power spectral analysis of the typical noise floor of the MAW sensor. Specifically, the typical noise floor of the MAW sensor, when left quietly on the phantom, is on the order of ~10$^{-4}$ g/Hz$^{1/2}$. At the output sound pressure level of 56 dB, the acoustic exciter produced sufficient MAW signals with a signal to noise ratio of 20 dB.

Figure 10:
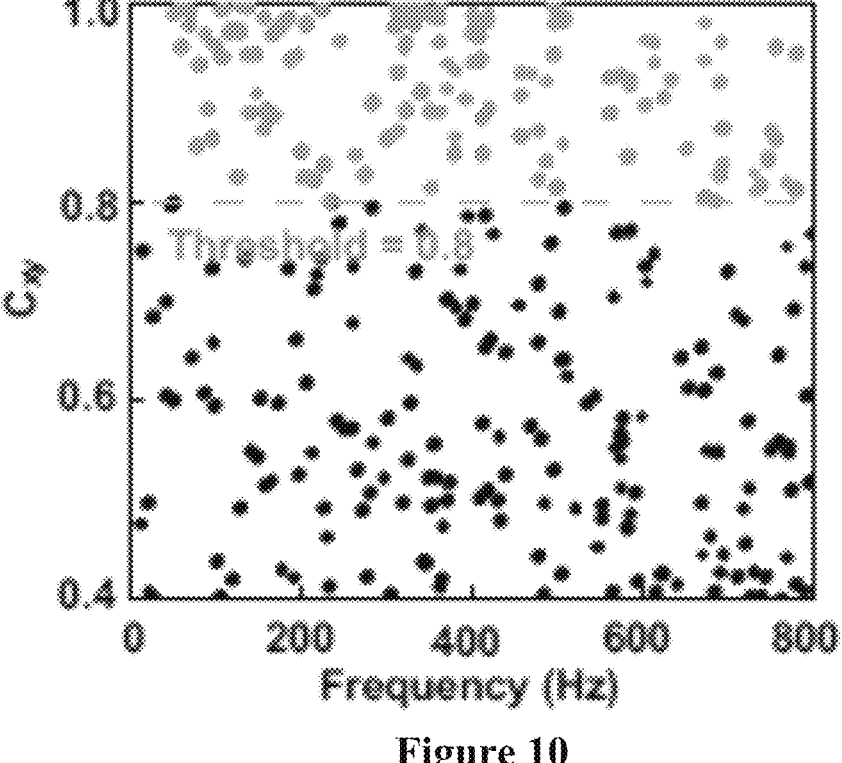
FIG. 10 illustrates a cross-power spectral analysis of measurements from the plurality of accelerometers in an experiment.
Figure 11:
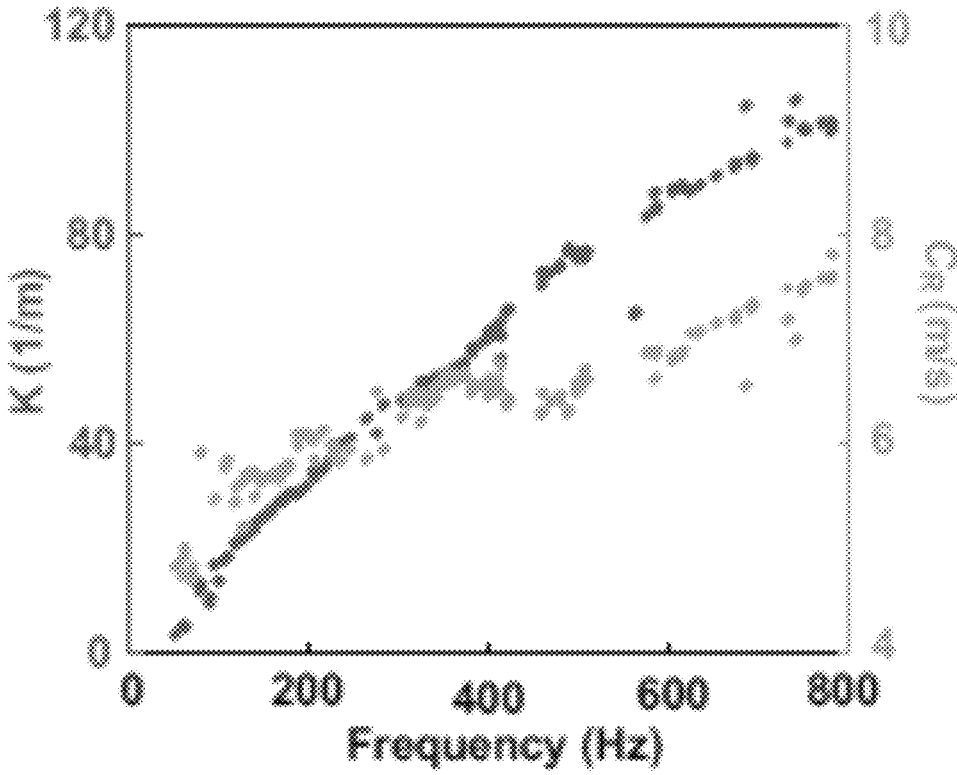
FIG. 11 illustrates the measured dispersion curves in an experiment.

FIG. 10 illustrates a cross-power spectral analysis of measurements from the plurality of accelerometers combined with a 0.8 coherence threshold to filter noisy frequency components to provide the frequency-dependent, unwrapped phase lag $\phi(f)$, with f representing the wave frequency. FIG. 11 illustrates the measured dispersion curves (i.e., frequency-dependent phase velocity $C_R(f)$ or wave number k(f)), given the measured phase lag $\phi(f)$ and the known distance D between each of the plurality of accelerometers (e.g., two accelerometers), which is represented as:

$$C_R(f) = \frac{D_f}{\phi(f)}; K(f) = \frac{\phi(f)}{D} \qquad [1]$$

Where $C_R$ relates to the Young's modulus (E), Poisson ratio (v), and mass density ($\rho$) of the propagating media approximately as:

$$C_R(f) = \frac{0.862 + 1.14v}{1 + v}c(f) \qquad [2]$$

Where the shear wave velocity c(f) correlates to the elasticity of an isotropic, incompressible and homogenous material as:

$$c(f) = \sqrt{\frac{E(f)}{2(1 + v)p}} \qquad [3]$$

Where E(f) is the Young's modulus at different frequencies and $\rho$ is the mass density. The inventors assumed that human tissues are incompressible with $\rho$=1.05 g/cm$^3$ and v=0.5[39] and close-to-zero dissipation, which the model estimated the Young's modulus of the dispersive media to be E(f)=3 pc(f)$^2$.

Scaling Law and Young's Modulus Derivation

Figures 12, 13A, 13B:
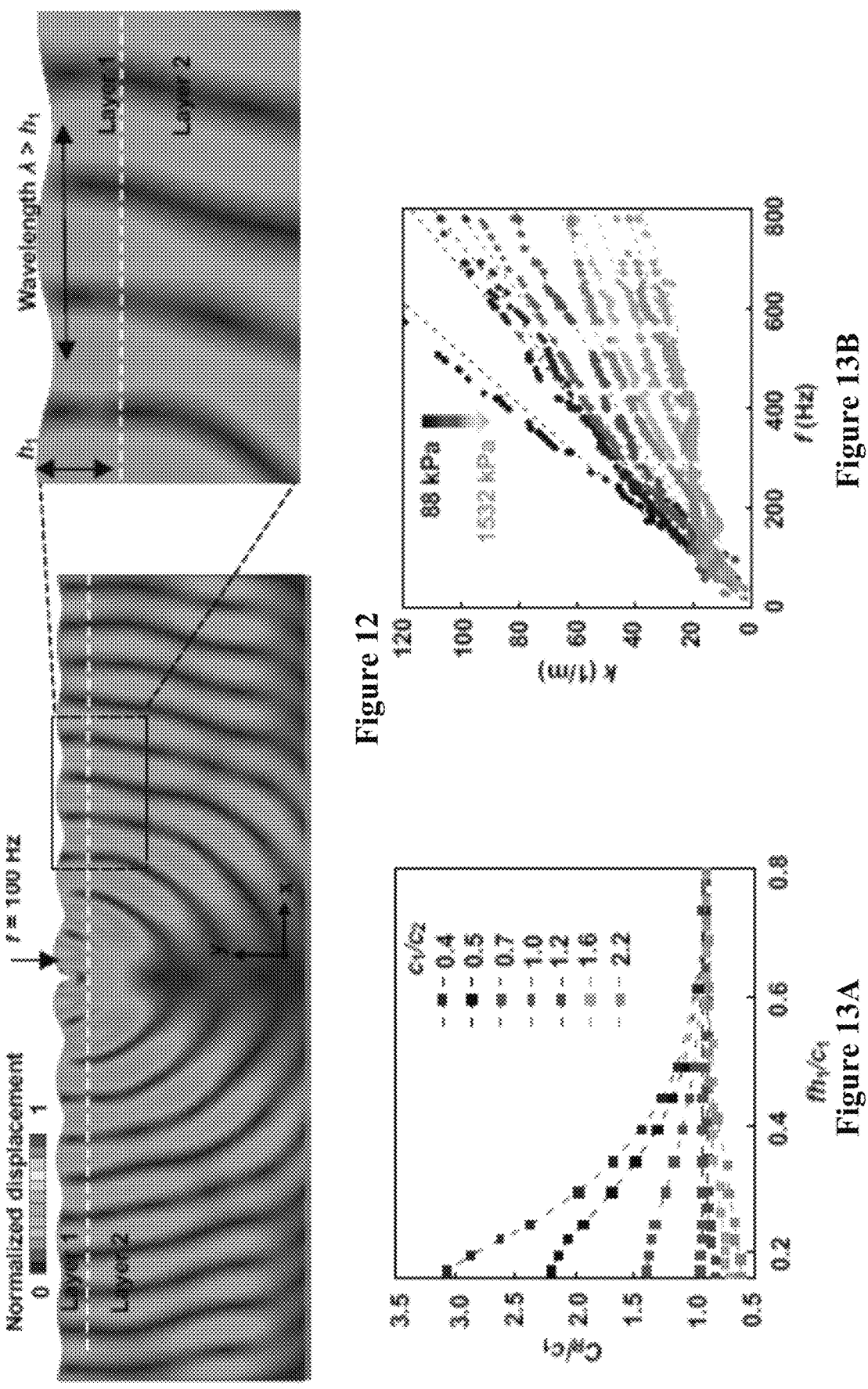
FIG. 12 illustrates the FEA prediction of y-axis displacement as an excited Raleigh wave propagates in the bi-layer material along the x-axis in an experiment.
FIG. 13A illustrates that the nondimensional surface wave velocity is a constant.
FIG. 13B illustrates the dispersion curves measured from 10 different custom-made, bi-layer phantom materials.

FEA provided a mechanical model for the bi-layer system. FIG. 12 illustrates the FEA prediction of y-axis (e.g., vertical to the surface) displacement as an excited Raleigh wave propagates in the bi-layer material M2 along the x-axis (e.g., parallel to the surface), actuated by a periodic point force at a frequency of 100 Hz. Spatial Fourier analysis gave the surface wave velocity $C_R$ at the actuation frequency. Repeating the process for different frequencies led to the dispersion relation between $C_R$ and f. Dimensional analysis using the FEA-derived dispersion established a scaling law relating the nondimensional velocity $C_R/c_1$, the nondimensional frequency $fh_1/c_1$, and the ratio of shear wave velocity $c_1/c_2$ as:

$$\frac{C_R}{c_1} = F\left(\frac{fh_1}{c_1}, \frac{c_1}{c_2}\right) \qquad [4]$$

Where the subscripts denote the parameters for Layer i and i=1, 2. FIG. 13A suggests that the nondimensional surface wave velocity is a constant ($C_R/c_1$=0.95) at sufficiently high frequencies $f_0$, for $f_0h_1/c_1$>0.6. These high-frequency waves exhibited characteristics akin to those in a homogeneous material, which enabled the estimation of $c_1$ as the average of $C_R(f>f_0)/0.95$. Consequently, $E_1$ was determined as 3pc$_1{}^2$. Lower-frequency waves ($\lambda$>$h_1$) penetrated deeper layers below the bi-layer interface and the wave characteristics became non-trivial. Minimizing the sum of squared differences between experimental measurement ($C_R$) and theoretical prediction ($C_R'$) at all frequencies yielded an estimation on $h_1$, $c_2$ as:

$$h_1, c_2 = \text{argmin}\left(\sum_{f=f_{min}}^{f_{max}} [C_R'(f) - C_R(h_1, c_2 \mid f, c_1)]^2\right) \qquad [5]$$

Based on $c_2$, $E_2$ can be determined as $3\rho c_2{}^2$.

Figure 13C:
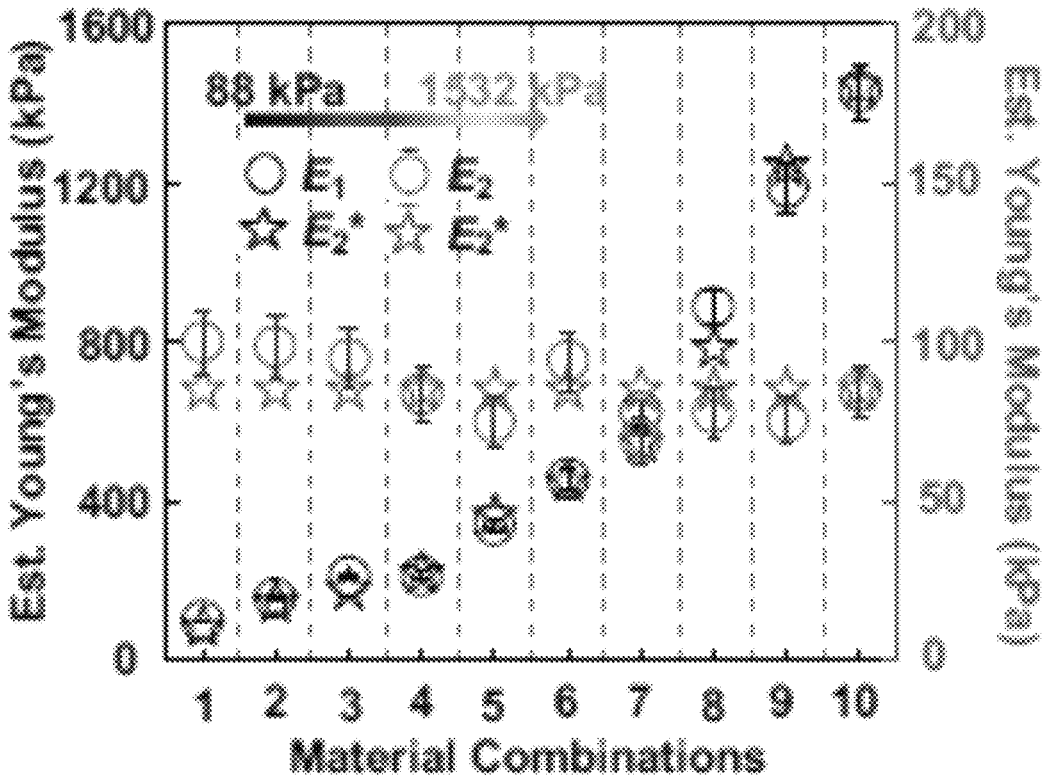
FIG. 13C illustrates the dispersion curves from the experiments are consistent with the FEA predictions within an absolute mean error of 10%.

FIG. 13B illustrates the dispersion curves measured from 10 different custom-made, bi-layer phantom materials. The materials share the same bottom substrate but have a different bottom-layer material, with $$E_1^* = 88\text{--}1532 \text{ kPa}, E_2^* = 90 \text{ kPa}, h_1^* = 10 \text{ mm}, h_2^* = 80 \text{ mm}$$

and where $E^*$ and $h^*$ are the ground truth modulus and depth values of the top and bottom layer materials estimated from tensile tests (TA Instrument, RSA G2) and a caliper. FIG. 13C illustrates the dispersion curves from the experiments are consistent with the FEA predictions within an absolute mean error of 10%. The measured $E_1$ and $E_2$ agreed with the ground-truth results with a mean error of 9%. The estimated depth of the top layer materials, $h_1$, agreed with the measurements from a caliper with 6% mean error. MAW measurements on 9 additional bi-layer phantom materials with the same top layer but different bottom layers, where $$E_1^* = 205 \text{ kPa}, E_2^* = 99\text{--}732 \text{ kPa}, h_1^* = 10 \text{ mm}, h_2^* = 10 \text{ mm},$$

revealed a mean error of 10% in estimated modulus and a mean error of 9% in estimated depth. The variations in estimations agree with a statistical analysis using simulated errors in the dispersion curves.

Tests on a phantom material (e.g., a mixture of Ecoflex and Dragon-skin with a weight ratio of 2:1, Young's modulus of 147 kPa, 20 mm thick, and 135 mm in length) curved with a surface radius of 5.5 cm or uniaxially stretched to 10% engineering strain, gave an estimated modulus with 10% difference from the tensile test. The modulus estimation from tests under vibration with amplitude of on a vortex mixer *Vortex-Genie2, Scientific Industries) was within 5% difference from the tensile test.

Validation Tests on Synthetic and Porcine Tissues

Measurements on synthetic tissues, conducted simultaneously with ShearWave™ Elastography (SWE; Siemens ACUSON Sequoia, 18L6 transducer), demonstrated the utility of the MAW in analyzing biomaterials with layered structures. An initial benchmark test on an ultrasound phantom made from hydrogel polymer (Zerdine, 040GSE) confirmed the agreement between the MAW and SWE estimation of elastic modulus within 5% error.

Figure 14A:
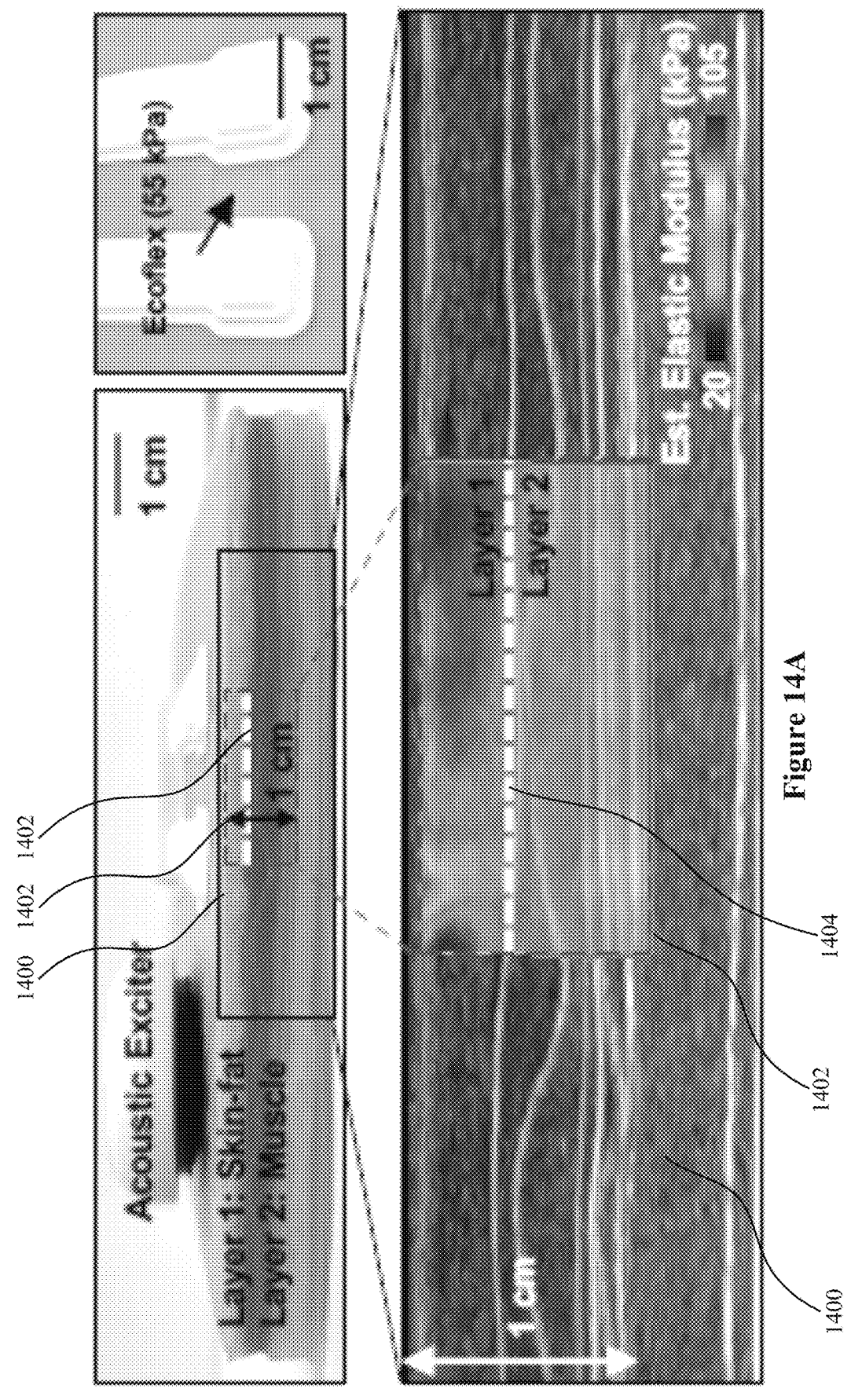
FIG. 14A illustrates a cross-sectional image of the experimental setup, with the region of interest for ultrasound imaging and modulus mapping enhanced underneath of the artificial tissue.
Figure 14B:
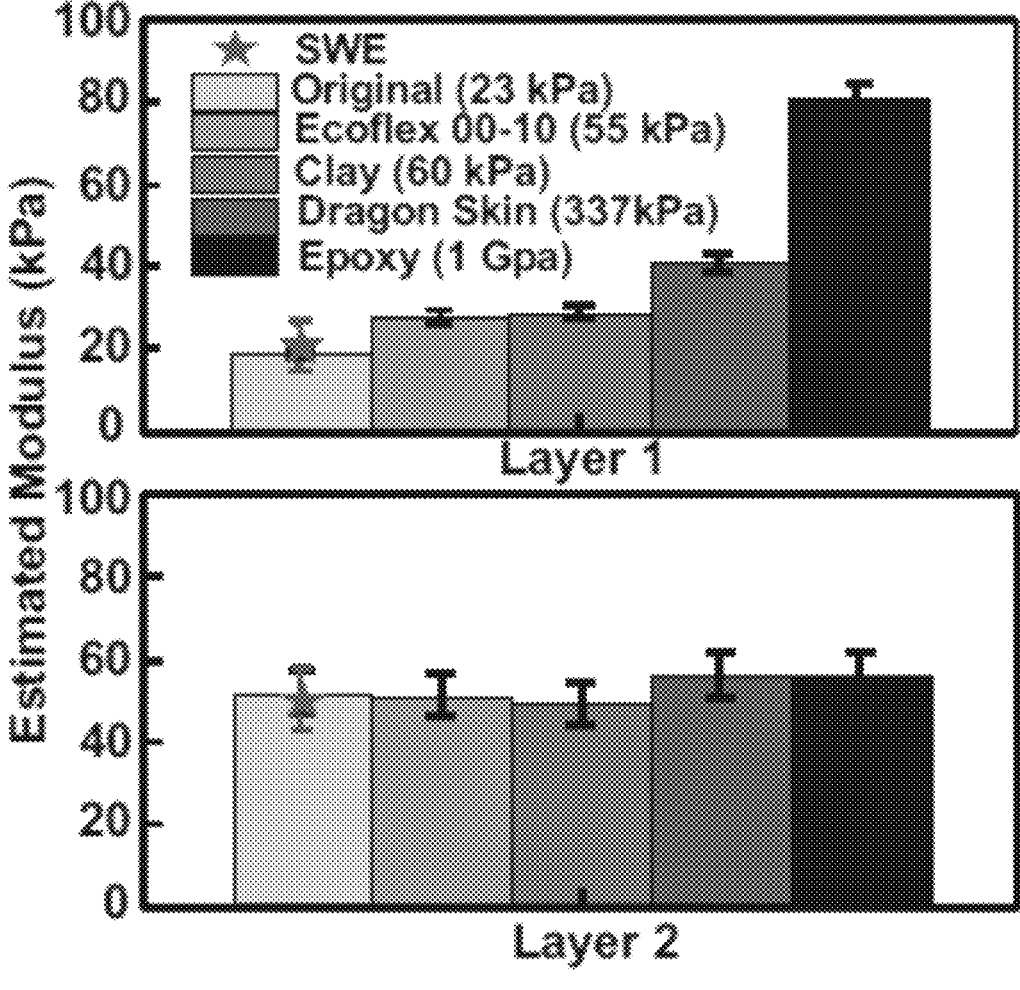
FIG. 14B illustrates the MAW measurement of the modulus.

An artificial tissue analog (Abdominal Tissue Plate, Syn-Daver) featuring multilayer structures served as a skin-fat and muscle-organ tissue model for simulating different types of skin/tissue disorders for the MAW to detect. FIG. 14A illustrates a cross-sectional image of the experimental setup, with the region of interest for ultrasound imaging and modulus mapping enhanced underneath of the artificial tissue. The dimensions of the region of interest 1400 of the artificial tissue is 10 mm in length, 10 mm in width, and 1 mm in height and was composed of phantom materials with different modulus (55-1000 kPa) embedded in the skin-fat layer to simulate a range of skin lesions. The enhanced area 1402 illustrates the corresponding ultrasound image of the region of interest 1400 with a modulus map. The dashed line 1404 at 3.7 mm depth visually guided the interface between the top skin-fat and underneath muscle-organ layers. The averaged modulus obtained from the SWE in the two layers are $E_1$=23±7 kPa and $E_2$=51±8 kPa. In agreement, FIG. 14B illustrates the MAW measurement of the modulus are $E_1$=19±2 kPa and $E_2$=52±5 kPa with an estimated thickness of the skin-fat layer, $h_1$=4±0.4 mm. The modulus of Layer 1 measured by the MAW sensor is 28±2 kPa with the embedment of Ecoflex 00-10, 29±2 kPa with modeling clay, 41±2 kPa with Dragon-skin 00-10, and 81±4 kPa with epoxy, while Layer 2 remained relatively unchanged at 53±8 kPa.

Figures 15A, 15B, 15C, 15D:
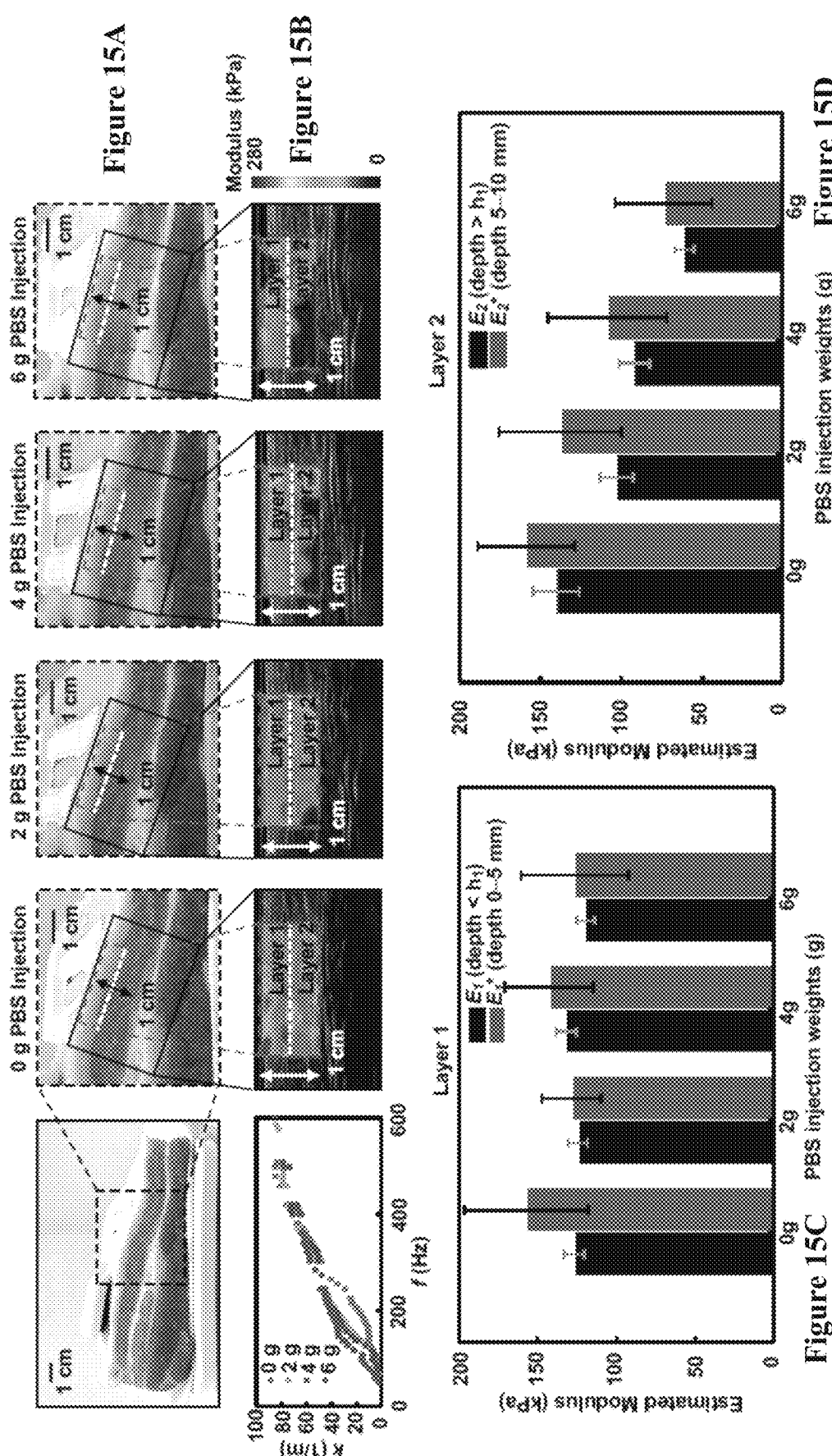
FIG. 15A illustrates the measurement setup on a 530 g skinless pork tissue with injections of PBS.
FIG. 15B illustrates that upon a single-point needle injection below the sensor into the muscle-organ layer, SWE shows that on average, the modulus of the top skin-fat layer remains relatively constant, while the underneath muscle-organ layer softens with increasing levels of water content.
FIG. 15C illustrates the top layer modulus measured from a MAW device compared with the top layer modulus measured from SWE.
FIG. 15D illustrates the bottom layer modulus measured from a MAW device compared with the bottom layer modulus measured from SWE.

Porcine tissue with weight-controlled injection of phosphate-buffered saline (PBS) provided an in-vitro edema model, for which an objective assessment is challenging. FIG. 15A illustrates the measurement setup on a 530 g skinless pork tissue with injections of PBS. The region below the sensor has a 4.1 mm thick subcutaneous fat layer on top of a muscle layer. Weight controlled injection of PBS simulated the progression of edema. Upon injection of 0 g, 2 g, 4 g, and 6 g PBS into the region below the sensor in the muscle layer, modulus measurements using the MAW sensor and SWE were conducted in series each time. FIG. 15B illustrates that upon a single-point needle injection of 0 g, 2 g, 4 g, and 6 g PBS 7 mm below the sensor into the muscle-organ layer, SWE shows that on average, the modulus of the top skin-fat layer stays close to 138.5 kPa with a variation of 30 kPa, while the underneath muscle-organ layer softens from 158.8 to 73.7 kPa with increasing levels of water content. The top-layer (e.g., as illustrated in FIG. 15C) and bottom-layer (e.g., as illustrated in FIG. 15D) modulus measured from the MAW device exhibit comparable values with the SWE results averaged from depth ranges of 0-5 mm and 5-10 mm. The estimated skin-fat layer thickness $h_1$ from MAW varies between 4 mm and 6 mm.

In-Vivo Testing Modulus Monitoring

Figures 16J, 17:
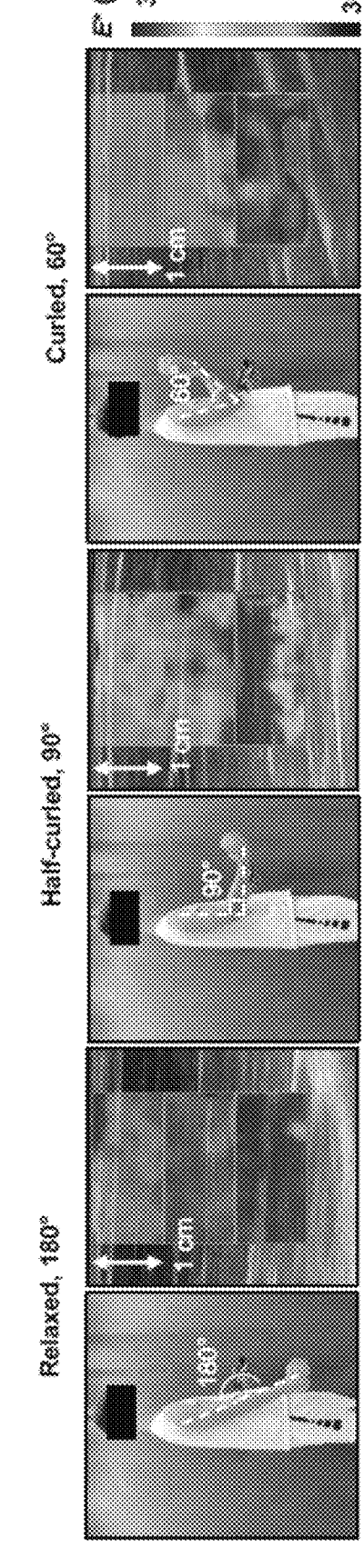
FIG. 16J illustrates the MAW measurements with a similar increasing trend with increasing weights as the SWE measurements.
FIG. 17 illustrates a healthy, normal subject (male 26 years old) wearing a MAW device on the right bicep during an experiment.

Testing on the skeletal muscle of a healthy, normal subject (e.g., male, 26 years old) provided in-vivo results. The test subject sat in a chair and positioned the forearm with an elbow angle of 60° while hand-holding objects of different weights (e.g., 0 g, 274 g, 465 g, 692 g, 1247 g, 2041 g, 3864 g, and 4535 g) to change the activation level of bicep brachii. FIG. 16A illustrates the experimental setup. FIGS. 16B-I illustrate the corresponding ultrasound images of the tissue underneath the sensor when the subject holds different weights. FIG. 16J illustrates the MAW measurements with a similar increasing trend from 55±5 kPa to 741±74 kPa with increasing weights as the SWE measurements.

Testing during gym exercises demonstrate the continuous monitoring capability of the MAW device during physical activities involving large deformation of skin. FIG. 17 illustrates a healthy, normal subject (male 26 years old) wearing a MAW device on the right bicep. For dynamic tests, an audio exciter an audio amplifier (ASX02604-R, PUI Audio; diameter=26.5 mm, weight=10 g) connecting the exciter and the Bluetooth receiver ensured adequate excitation. For the cyclic lifting test, the test subject lifted held a dumbbell in a relaxed (e.g., 180°) position for 10 seconds, followed by holding the dumbbell in a half-curled (e.g., 90°) position for another 10 seconds, followed by a holding the dumbbell in a curled (e.g., 60°) for another 10 seconds. Ultrasound imaging provided the SWE measurements of the bicep at the three static postures, serving as the ground truth. The averaged modulus in the depth range of 0-10 mm and 20-30 mm were $E^*_{relaxed,\ 0\text{-}10\ mm}=88\pm31$ kPa and $E^*_{relaxed,\ 20\text{-}30\ mm}=47\pm8$ kPa, $E^*_{half\text{-}curled,\ 0\text{-}10\ mm}=221\pm39$ kPa and $E^*_{half\text{-}curled,\ 20\text{-}30\ mm}=323\pm94$ kPa, and $E^*_{curled,\ 0\text{-}10\ mm}=121\pm24$ kPa and $E^*_{curled,\ 20\text{-}30\ mm}=52\pm11$ kPa for the three postures. The MAW device was tested with the same parameters and further added seven cycles of curls using the dumbbell for a final 30 seconds. The results of the MAW device for this test are illustrated in FIGS. 6A and 6B. The bi-layer model recorded the continuous change in tissue stiffness during both the holding (e.g., 0-30 seconds) and the cycling tests (e.g., 30-60 seconds). In the 30 second holding test, the MAW measurements captures the modulus transition from the relaxed posture ($E_{relaxed,\ 1}=100\pm11$ kPa and $E_{relaxed,\ 2}=48\pm8$ kPa) to the half-curled posture ($E_{half\text{-}curled,\ 1}=256\pm36$ kPa and $E_{half\text{-}curled,\ 2}=331\pm53$ kPa) to the curled posture ($E_{curled,\ 1}=134\pm7$ kPa and $E_{curled,\ 2}=58\pm9$ kPa). The results closely match the SWE results (e.g., as illustrated in FIG. 6B), with a maximum error of 16%. The estimated thickness of Layer 1 remains relatively stable at around 17 mm in each posture throughout the test. The muscle modulus reached the local maxima around the half-curled posture ($E_{half\text{-}curled,\ 1}=320\pm60$ kPa and $E_{half\text{-}curled,\ 2}=474\pm67$ kPa) and local minima at the relaxed ($E_{relaxed,\ 1}=251\pm25$ kPa and $E_{relaxed,\ 2}=359\pm35$ kPa) and curled ($E_{curled,\ 1}=106\pm22$ kPa and $E_{curled,\ 2}=55\pm29$ kPa) postures. The modulus of Layer 2 underwent larger changes in modulus than that of Layer 1 during the cycles. Similar tests on the rectus femoris muscle of the same subject demonstrated a robust performance of the MAW device during leg-pressing exercise. These real-time tests showcased the MAW sensor's ability to enable continuous, on-body monitoring of muscle stiffness during movement, which is unattainable with conventional ultrasound elastography.

Discussion

The resulting MAW device and system enables the robust, calibration-free, and non-invasive evaluation of the elasticity on soft materials and tissues, covering a modulus of 20-1532 kPa with a mean error of less than 10% and an estimated depth of 2-46 mm. Both in-vitro and in-vivo tests showed quantitative agreement with parallel ultrasound elastography measurements without any calibration, demonstrating an unprecedented balance between ease of use, accuracy, and cost. The results from the experiment validate the MAW device's clinical potential in assessing the mechanical states of tissues without the need for expensive equipment and/or dedicated personnel. The unique capabilities of continuous measurement during dynamic motions with a temporal resolution of 1600 Hz or even beyond. Power consumption of current proof-of-concept MAW device is at 10 mA, which equates to 6 hours of continuous operation.

The potential clinical applications include, but are not limited to, skin cancer, muscle loading, wound-healing, and tissue regeneration. The MAW device provides a cost-effective and convenient tool to study the effects of ageing, hydration levels, and associated disorders on the soft tissues. The MAW device is meaningful not only for diagnostic purposes but also for the evaluation of therapy efficacy to generate novel therapeutic targets, as well as for research and tissue engineering of disease in in-vitro models.

Methods

Fabrication of the MAW device included patterning a sheet of fPCB (18 μm-thick top and bottom Cu layer, 75 μm middle polymide layer) into the pre-designed shapes using an ultraviolet laser cutter (U4, LPKF). The serpentines that connect the accelerometers and the main electronic board had a width of 0.65 mm, a length of 36 mm, and an arc angle of 270°, and supported four 150 μm-wide copper traces on each of them. The Bluetooth System on Chip (nRF52832, Nordic Semiconductor), two accelerometers (MPU9250, InvenSense), flash memory (W25Q128, Winbond), low dropout voltage regulator (LP5907, Texas Instrument), slide switch (JS102011JCON, C&K) and passive components (resistors, capacitors and inductors) were bonded to the fPCB via reflow solder using solder paste (TS391LT, Chip Quik) and a heat gun (861DQ, Quick).

The assembled fPCB was encapsulated by a soft silicone material (Silibone RTV 4420, Elkem) with or without 3% white silicone dyes (SilcPig, Smooth-On) for a white or transparent appearance. The top encapsulation layer (0.5 mm thickness) was formed via compression molding with two aluminum molds designed in SolidWorks and fabricated using a three-axis milling machine (MDX 540, Roland). The bottom encapsulation layer (0.2 mm thickness) was obtained on a glass slide via spin-coating. To encapsulate the device, uncured silicone was used as an adhesive to bond the fPCB and the bottom encapsulation layer, as well as the top and bottom encapsulation layers. A customized cutting die (Millenium Die Group) defined the outline of the final encapsulated device.

A 3D printer (Form 3, Formlabs) created the protection casing for the acoustic receiver (ASX02604-R, PUI Audio). The audio exciter was connected to a Bluetooth audio receiver (MG-X2, Hagibis) using a 3.5 mm audio cable. Audio signals were played by a smart device connected to the receiver via Bluetooth. For in-vivo dynamic muscle tests, an additional audio amplifier (AMP2X15, PUI Audio) was connected between the audio exciter and the Bluetooth receiver and was enclosed with the battery by a 3D-printed housing for protection and portability.

Bi-layer phantom materials were fabricated by mixing different weight ratios of Ecoflex 00-30 (SmoothOn) and Dragon-skin 00-10 (SmoothOn) elastomers or different weight ratios of the polydimethysiloxane (PDMS) base and curing agent (Sylgard 184, Dow). Samples were molded in petri dishes (100 mm diameter and 10 mm thickness).

Tensile test (RSA G2, TA Instrument) used a film tension clamp at 25° C. with a range of prescribed small strains (<3%), both loading and unloading strain rates are $5\times10^{-1}$ $s^{-1}$. Samples for tensile tests were cut into size of 20 mm×5 mm×1 mm (length×width×thickness).

A synthetic tissue analog (Abdominal Tissue Plate, Syn-Daver) was used to construct skin lesion models. A box of size 10 mm×10 mm×1 mm was cut off using a scapel from the top center of the tissue model. Modeling clay (Crayola LLC), Ecoflex 00-30 (SmoothOn), Dragon-skin 00-10 (SmoothOn), or epoxy (Scotch-Weld, 3M) were cured in the box.

FEA was performed using the commercial software ABAQUS. For the simulation of mechanical deformation (stretching, bending, and twisting), the MAW device and encapsulation layer were modeled with hexahedron elements (DC3D8). A refined mesh with the dimension of ¼ of the finest feature size of the device (18 μm, top and bottom copper thickness) was adopted to guarantee simulation convergence and accuracy. For the simulation of the wave propagation in bi-layer models, a periodic point force was used for actuating surface waves. Infinite boundaries were used to mimic the real on-body environments while excluding the influence of reflection waves. Refined mesh with the dimension of $1/40$ of the minimum of the smallest wavelength, the thickness of the top layer, and the thickness of the bottom layer was adopted to guarantee the simulation convergence and accuracy.

For the calculation of the signal noise ratio, 2 seconds of data underwent spectrum analysis using a Hanning window of 1.8 seconds moving in time steps of 0.6 seconds. The cross-power spectral analysis of dual-accelerometer measurements used a Hanning window of 0.8 seconds moving in time steps of 0.4 seconds, and gave the wrapped phase lag $\Delta\varphi(f)$ with a range of $-\pi$ to $\pi$. Adding the proper number of $2\pi$ to $\Delta\varphi(f)$ for each frequency gave the unwrapped phase lag $\varphi(f)$. The phase data at frequencies with coherence higher than 0.8 were used to construct the dispersion curves. Phase zero was calibrated by measurements with the accelerometers stacked together on the acoustic exciter. A wired device with two analog accelerometers (ADXL 326, Analog Devices, Inc.) sampled at 10,000 Hz was used for the ground-truth comparison.

A commercial ShearWave™ Elastography system (SWE; Siemens ACUSON Sequioa, 18L6 transducer) was used to validate the MAW device. An operational frequency of 5.3 MHz was used for the push excitation, and a track transmit frequency of 6.7 MHz was used for the measurement of shear wave velocities. Shear wave speed maps were placed and superimposed into ultrasound for ground-truth comparison.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:

1. A wearable device comprising:
an elastically compliant body having a side for attaching to skin of a patient;
a plurality of accelerometers for receiving acoustic wave data from acoustic waves transmitted by a transducer, wherein a distance between each accelerometer of the plurality of accelerometers is predetermined;
a short-range radio transmitter for transmitting the acoustic wave data to a computing device;
a processor for receiving the acoustic wave data from the plurality of accelerometers and providing the acoustic wave data to the short-range radio transmitter; and
a battery for providing power to the processor, the plurality of accelerometers, and the short-range radio transmitter,
wherein the processor, the plurality of accelerometers, the short-range radio transmitter, and the battery are embedded within the elastically compliant body.

2. The wearable device of claim 1, further comprising a strain gauge that is coupled to each of the plurality of accelerometers for measuring real-time distance between each of the plurality of accelerometers.

3. The wearable device of claim 1, further comprising a memory for on-board storage of the acoustic wave data received by the plurality of accelerometers.

4. The wearable device of claim 1, wherein the short-range radio transmitter and the processor are part of a System-on-Chip.

5. The wearable device of claim 1, further comprising the transducer for transmitting the acoustic waves.

6. The wearable device of claim 5, wherein the transducer is embedded within the elastically compliant body at second distance from the plurality of accelerometers that is predetermined.

7. The wearable device of claim 5, wherein the transducer is an audio exciter.

8. A system comprising:
a transducer for transmitting acoustic waves;
a wearable device comprising:
an elastically compliant body having a side for attaching to skin of a patient;
a plurality of accelerometers for receiving acoustic wave data from acoustic waves transmitted by a transducer, wherein a distance between each accelerometer of the plurality of accelerometers is predetermined;
a short-range radio transmitter for transmitting the acoustic wave data to a computing device;
a processor for receiving the acoustic wave data from the plurality of accelerometers and providing the acoustic wave data to the short-range radio transmitter; and
a battery for providing power to the processor, the plurality of accelerometers, and the short-range radio transmitter,
wherein the processor, the plurality of accelerometers, the short-range radio transmitter, and the battery are embedded within the elastically compliant body; and
one or more storage media having instructions stored thereon that when executed by a processing system, direct the processing system to at least:
store, at a computing device, a model of a wearable device having a plurality of accelerometers, the model comprising a distance value between each accelerometer of the plurality of accelerometers;
send, from the computing device, a signal to a transducer to transmit acoustic waves into a body;
receive, over a wireless protocol from the wearable device, acoustic wave data captured from the acoustic waves transmitted into the body;
measure a phase lag of the acoustic wave data;
determine a frequency-dependent phase velocity from the acoustic wave data based on the measured phase lag and the distance value between each accelerometer of the plurality of accelerometers of the wearable device;
determine a shear wave velocity based on the frequency-dependent phase velocity and a predetermined incompressible mass density;
determine tissue stiffness of tissue in the body that the acoustic waves pass through based on the shear wave velocity; and
cause to display the determined tissue stiffness in a graphical user interface of the computing device.

9. The system of claim 8, wherein the wearable device further comprises a strain gauge that is coupled to each of the plurality of accelerometers for measuring real-time distance between each of the plurality of accelerometers.

10. The system of claim 8, wherein the wearable device further comprises a memory for on-board storage of the acoustic wave data received by the plurality of accelerometers.

11. The system of claim 8, wherein the transducer is an audio exciter.

12. The system of claim 8, wherein the model is updated with a real-time distance value between each accelerometer of the plurality of accelerometers while the wearable device is in use.

13. The system of claim 8, wherein no calibration to the wearable device is required to determine the tissue stiffness.

14. A method comprising:

storing, at a computing device, a model of a wearable device having a plurality of accelerometers, the model comprising a distance value between each accelerometer of the plurality of accelerometers;

sending, from the computing device, a signal to a transducer to transmit acoustic waves into a body;

receiving, over a wireless protocol from the wearable device, acoustic wave data captured from the acoustic waves transmitted into the body;

measuring a phase lag of the acoustic wave data;

determining a frequency-dependent phase velocity from the acoustic wave data based on the measured phase lag and the distance value between each accelerometer of the plurality of accelerometers of the wearable device;

determining a shear wave velocity based on the frequency-dependent phase velocity and a predetermined incompressible mass density;

determining tissue stiffness of tissue in the body that the acoustic waves pass through based on the shear wave velocity; and causing to display the determined tissue stiffness in a graphical user interface of the computing device.

15. The method of claim 14, wherein no calibration to the wearable device is required to determine the tissue stiffness.

16. The method of claim 14, wherein the tissue stiffness is determined in real time and displayed in real time over a time period.

17. The method of claim 16, wherein the wearable device is attached to skin of a patient that is engaged in physical activity or in an ambulatory setting.

18. The method of claim 14, wherein the wireless protocol is Bluetooth Low Energy protocol.

19. The method of claim 14, wherein the model is updated while the wearable device is in use.

20. The method of claim 19, wherein the update to the model is an update to the distance value between each accelerometer of the plurality of accelerometers sent from the wearable device.

* * * * *